(12) United States Patent
Uden et al.

(10) Patent No.: US 6,783,981 B1
(45) Date of Patent: Aug. 31, 2004

(54) ANTI-VIRAL VECTORS

(75) Inventors: Mark Uden, London (GB); Kyriacos Mitrophanous, Oxford (GB)

(73) Assignee: Oxford Biomedica (UK) Limited, Oxford (GB)

(*) Notice: Subject to any disclaimer, the term of this patent is extended or adjusted under 35 U.S.C. 154(b) by 0 days.

(21) Appl. No.: 09/936,572

(22) PCT Filed: Mar. 17, 2000

(86) PCT No.: PCT/GB00/01002

§ 371 (c)(1),
(2), (4) Date: Dec. 11, 2001

(87) PCT Pub. No.: WO00/55341

PCT Pub. Date: Sep. 21, 2000

(30) Foreign Application Priority Data

Mar. 17, 1999 (GB) .............................................. 9906177

(51) Int. Cl.[7] .......................... C12N 5/00; C12N 15/64; C12N 15/00; C12Q 1/70; C12P 21/06
(52) U.S. Cl. .......................... 435/325; 435/5; 435/69.1; 435/91.4; 435/320.1; 435/455; 536/23.72
(58) Field of Search .............................. 435/325, 69.1, 435/91.4, 320.1, 455, 5; 536/23.72

(56) References Cited

U.S. PATENT DOCUMENTS 6,541,248 B1 * 4/2003 Kingsman et al. .......... 435/325

FOREIGN PATENT DOCUMENTS

| EP | 0 711 829 | 5/1996 |
|----|-----------|--------|
| WO | 97/20060 | 6/1997 |
| WO | 98/17815 | 4/1998 |
| WO | 99/41397 | 8/1999 |

* cited by examiner

Primary Examiner—Hankyel T. Park
(74) Attorney, Agent, or Firm—Frommer Lawrence & Haug; Thomas J. Kowalski; Anne Marie Yvon

(57) ABSTRACT

A viral vector production system is provided which system comprises: (i) a viral genome comprising at least one first nucleotide sequence encoding a gene product capable of binding to and effecting the cleavage, directly or indirectly, of a second nucleotide sequence, or transcription product thereof, encoding a viral polypeptide required for the assembly of viral particles, (ii) a third nucleotide sequence encoding said viral polypeptide required for the assembly of the viral genome into viral particles, which third nucleotide sequence has a different nucleotide sequence to the second nucleotide sequence such that said third nucleotide sequence, or transcription product thereof, is resistant to cleavage directed by said gene product; wherein at least one of the gene products is an external guide sequence capable of binding to and effecting the cleavage by RNase P of the second nucleotide sequence. The viral vector production system may be used to produce viral particles for use in treating or preventing viral infection.

22 Claims, 14 Drawing Sheets

Figure 1
pH4Rz
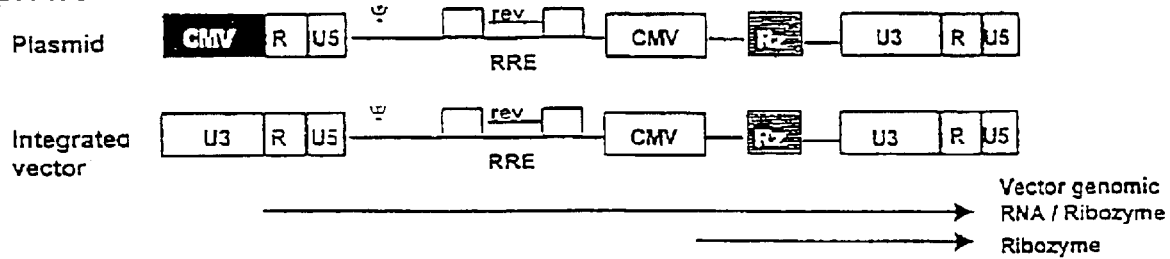
pH4.1Rz
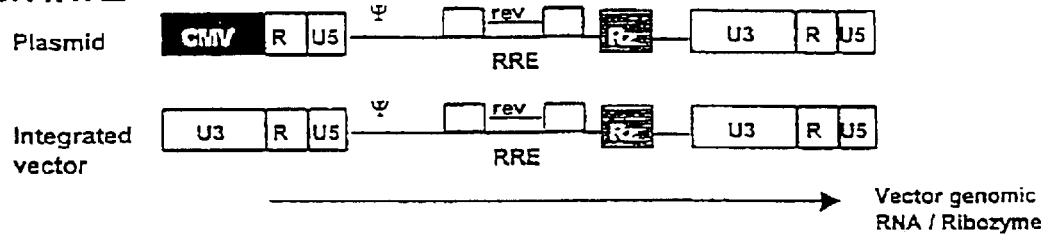
pH6Rz
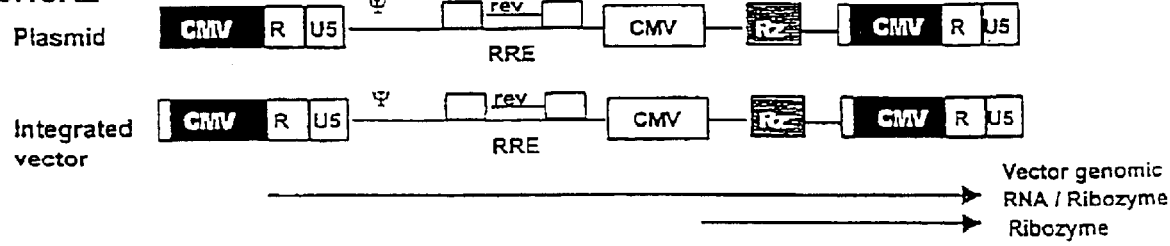
pH6.1Rz
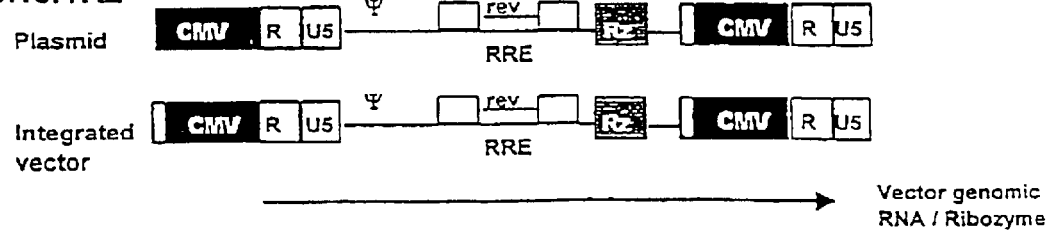

figure 2
A
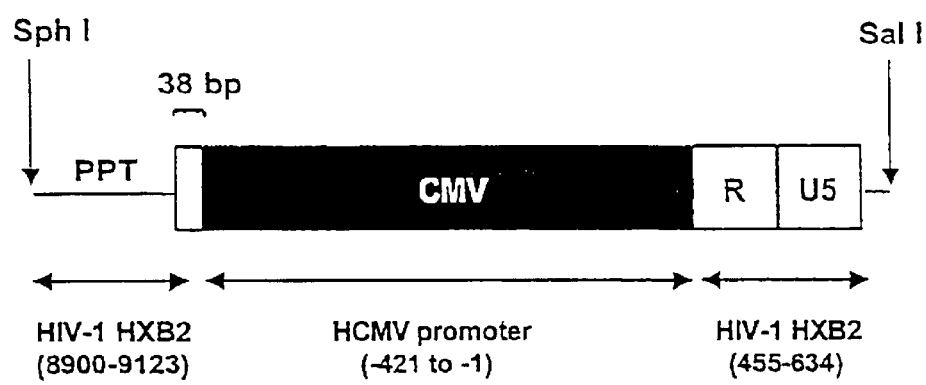
B
1' PCR from pH4
2' PCR from pH4
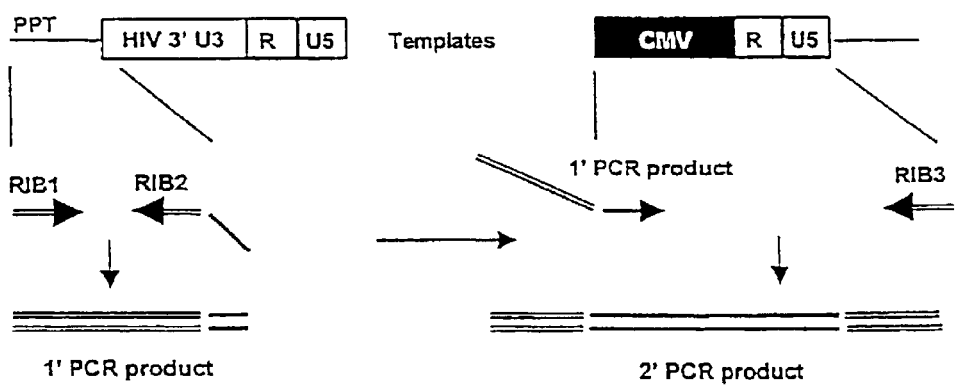

Figure 3 gagpol-HXB2 -> Codon Usage

DNA sequence   4308 b.p.   ATGGGTGCGAGA ... GATGAGGATTAG   linear 1436 codons

MW : 161929 Dalton    CAI(S.c.) : 0.083    CAI(E.c.) : 0.151

| TTT phe F | 21 | TCT ser S | 3  | TAT tyr Y | 30 | TGT cys C | 18 |
| TTC phe F | 14 | TCC ser S | 3  | TAC tyr Y | 9  | TGC cys C | 2  |
| TTA leu L | 46 | TCA ser S | 19 | TAA OCH Z | -  | TGA OPA Z | -  |
| TTG leu L | 11 | TCG ser S | 1  | TAG AMB Z | 1  | TGG trp W | 37 |
|           |    |           |    |           |    |           |    |
| CTT leu L | 13 | CCT pro P | 21 | CAT his H | 20 | CGT arg R | -  |
| CTC leu L | 7  | CCC pro P | 14 | CAC his H | 7  | CGC arg R | -  |
| CTA leu L | 17 | CCA pro P | 41 | CAA gln Q | 56 | CGA arg R | 3  |
| CTG leu L | 16 | CCG pro P | -  | CAG gln Q | 39 | CGG arg R | 3  |
|           |    |           |    |           |    |           |    |
| ATT ile I | 30 | ACT thr T | 24 | AAT asn N | 42 | AGT ser S | 18 |
| ATC ile I | 14 | ACC thr T | 20 | AAC asn N | 16 | AGC ser S | 16 |
| ATA ile I | 56 | ACA thr T | 43 | AAA lys K | 88 | AGA arg R | 45 |
| ATG met M | 29 | ACG thr T | 1  | AAG lys K | 34 | AGG arg R | 18 |
|           |    |           |    |           |    |           |    |
| GTT val V | 15 | GCT ala A | 17 | GAT asp D | 37 | GGT gly G | 11 |
| GTC val V | 11 | GCC ala A | 19 | GAC asp D | 26 | GGC gly G | 10 |
| GTA val V | 55 | GCA ala A | 55 | GAA glu E | 75 | GGA gly G | 61 |
| GTG val V | 15 | GCG ala A | 5  | GAG glu E | 32 | GGG gly G | 26 |

Figure 4 gagpol-SYNgp [1 to 4308] -> Codon Usage

DNA sequence    4308 b.p.    ATGGGCGCCCGC ... GATGAGGATTAG    linear 1436 codons MW : 161929 Dalton    CAI(S.c.) : 0.080    CAI(E.c.) : 0.296

| | | | | | | | | | | |
|---|---|---|---|---|---|---|---|---|---|---|
| TTT phe F | 5 | TCT ser S | 5 | TAT tyr Y | 10 | TGT cys C | 6 |
| TTC phe F | 30 | TCC ser S | 11 | TAC tyr Y | 29 | TGC cys C | 14 |
| TTA leu L | 2 | TCA ser S | 4 | TAA OCH Z | - | TGA OPA Z | - |
| TTG leu L | 7 | TCG ser S | 6 | TAG AMB Z | 1 | TGG trp W | 37 |
| | | | | | | | |
| CTT leu L | 3 | CCT pro P | 14 | CAT his H | 6 | CGT arg R | 2 |
| CTC leu L | 22 | CCC pro P | 39 | CAC his H | 21 | CGC arg R | 34 |
| CTA leu L | 6 | CCA pro P | 10 | CAA gln Q | 14 | CGA arg R | 3 |
| CTG leu L | 70 | CCG pro P | 13 | CAG gln Q | 81 | CGG arg R | 10 |
| | | | | | | | |
| ATT ile I | 17 | ACT thr T | 11 | AAT asn N | 13 | AGT ser S | 7 |
| ATC ile I | 79 | ACC thr T | 48 | AAC asn N | 45 | AGC ser S | 27 |
| ATA ile I | 4 | ACA thr T | 13 | AAA lys K | 25 | AGA arg R | 7 |
| ATG met M | 29 | ACG thr T | 16 | AAG lys K | 97 | AGG arg R | 13 |
| | | | | | | | |
| GTT val V | 5 | GCT ala A | 15 | GAT asp D | 19 | GGT gly G | 10 |
| GTC val V | 27 | GCC ala A | 56 | GAC asp D | 44 | GGC gly G | 54 |
| GTA val V | 6 | GCA ala A | 13 | GAA glu E | 29 | GGA gly G | 16 |
| GTG val V | 58 | GCG ala A | 12 | GAG glu E | 78 | GGG gly G | 29 |

Figure 5 env-mn (1 to 2571) -> Codon Usage

DNA sequence    2571 b.p.    ATGAGAGTGAAG ... GCTTTGCTATAA    linear 857 codons

MW : 97078 Dalton    CAI(S.c.) : 0.083    CAI(E.c.) : 0.140

| | | | | | | | | | | |
|---|---|---|---|---|---|---|---|---|---|---|
| TTT phe F | 13 | TCT ser S | 7 | TAT tyr Y | 15 | TGT cys C | 16 |
| TTC phe F | 11 | TCC ser S | 3 | TAC tyr Y | 7 | TGC cys C | 5 |
| TTA leu L | 20 | TCA ser S | 13 | TAA OCH Z | 1 | TGA OPA Z | - |
| TTG leu L | 17 | TCG ser S | 2 | TAG AMB Z | - | TGG trp W | 30 |
| | | | | | | | |
| CTT leu L | 9 | CCT pro P | 5 | CAT his H | 8 | CGT arg R | - |
| CTC leu L | 11 | CCC pro P | 9 | CAC his H | 6 | CGC arg R | 2 |
| CTA leu L | 12 | CCA pro P | 12 | CAA gln Q | 22 | CGA arg R | 1 |
| CTG leu L | 15 | CCG pro P | 2 | CAG gln Q | 19 | CGG arg R | 1 |
| | | | | | | | |
| ATT ile I | 21 | ACT thr T | 16 | AAT asn N | 50 | AGT ser S | 18 |
| ATC ile I | 10 | ACC thr T | 14 | AAC asn N | 13 | AGC ser S | 11 |
| ATA ile I | 32 | ACA thr T | 28 | AAA lys K | 32 | AGA arg R | 30 |
| ATG met M | 17 | ACG thr T | 5 | AAG lys K | 14 | AGG arg R | 15 |
| | | | | | | | |
| GTT val V | 8 | GCT ala A | 16 | GAT asp D | 18 | GGT gly G | 10 |
| GTC val V | 9 | GCC ala A | 7 | GAC asp D | 14 | GGC gly G | 6 |
| GTA val V | 26 | GCA ala A | 20 | GAA glu E | 36 | GGA gly G | 28 |
| GTG val V | 12 | GCG ala A | 5 | GAG glu E | 10 | GGG gly G | 12 |

Figure 6 syngp160mn -> Codon Usage

DNA sequence   2571 b.p.   ATGAGGGTGAAG ... GCGCTGCTGTAA   linear 857 codons

MW : 97078 Dalton   CAI(S.c.) : 0.074   CAI(E.c.) : 0.419

| | | | | | | | | |
|---|---|---|---|---|---|---|---|---|
| TTT phe F | - | TCT ser S | 2 | TAT tyr Y | 1 | TGT cys C | - |
| TTC phe F | 24 | TCC ser S | 4 | TAC tyr Y | 21 | TGC cys C | 21 |
| TTA leu L | - | TCA ser S | - | TAA OCH Z | 1 | TGA OPA Z | - |
| TTG leu L | - | TCG ser S | - | TAG AMB Z | - | TGG trp W | 30 |
| | | | | | | | |
| CTT leu L | - | CCT pro P | - | CAT his H | 2 | CGT arg R | 1 |
| CTC leu L | 20 | CCC pro P | 26 | CAC his H | 12 | CGC arg R | 36 |
| CTA leu L | 1 | CCA pro P | - | CAA gln Q | - | CGA arg R | - |
| CTG leu L | 63 | CCG pro P | 2 | CAG gln Q | 41 | CGG arg R | 4 |
| | | | | | | | |
| ATT ile I | 2 | ACT thr T | - | AAT asn N | 2 | AGT ser S | - |
| ATC ile I | 61 | ACC thr T | 59 | AAC asn N | 61 | AGC ser S | 48 |
| ATA ile I | - | ACA thr T | - | AAA lys K | 1 | AGA arg R | 2 |
| ATG met M | 17 | ACG thr T | 4 | AAG lys K | 45 | AGG arg R | 6 |
| | | | | | | | |
| GTT val V | - | GCT ala A | - | GAT asp D | 2 | GGT gly G | 1 |
| GTC val V | 1 | GCC ala A | 40 | GAC asp D | 30 | GGC gly G | 47 |
| GTA val V | 1 | GCA ala A | - | GAA glu E | 3 | GGA gly G | - |
| GTG val V | 53 | GCG ala A | 8 | GAG glu E | 43 | GGG gly G | 8 |

Figure 8
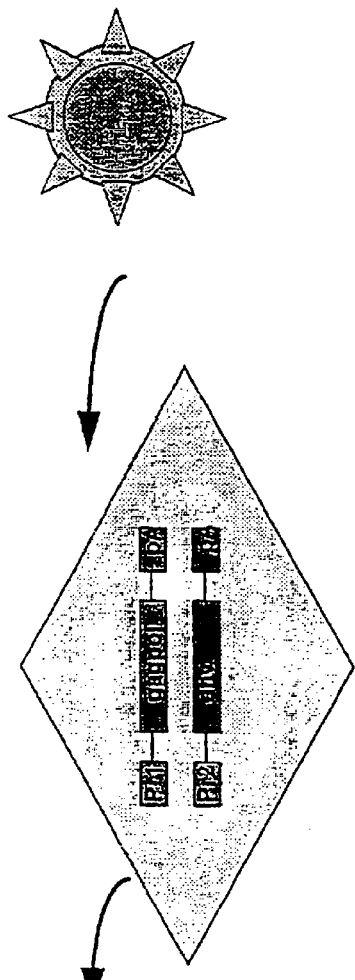
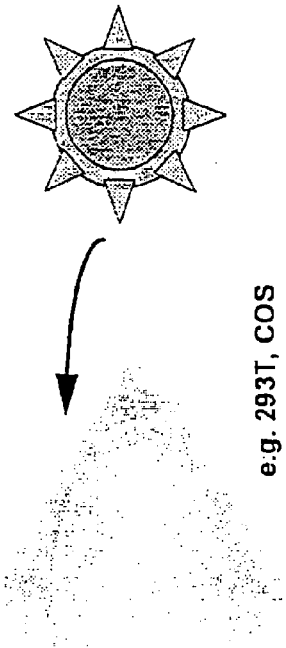

EGS Based on Tyrosyl t-RNA

Generic design of EGSs to target any RNA.

Figure 10 B
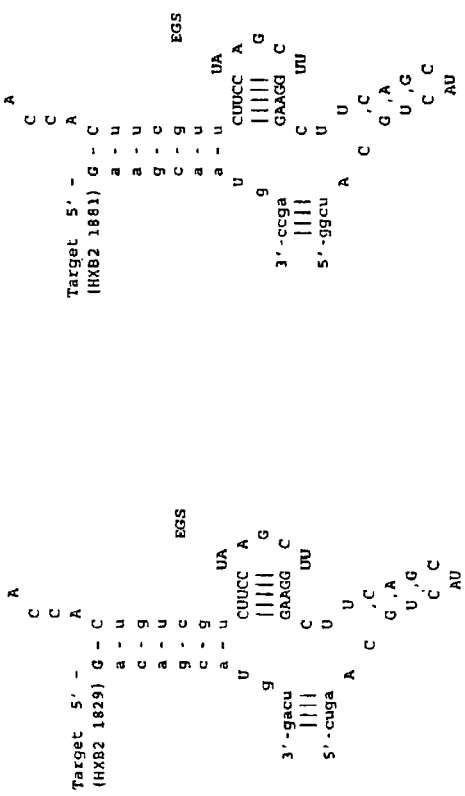
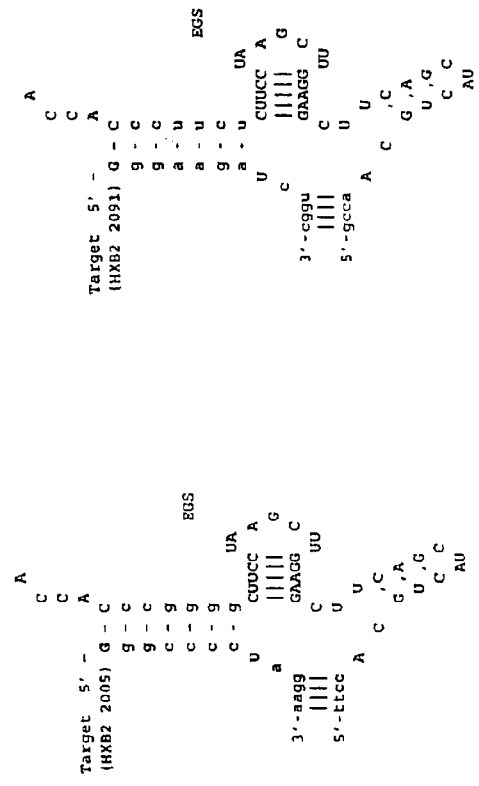

ANTI-VIRAL VECTORS

FIELD OF THE INVENTION

The present invention relates to novel viral vectors capable of delivering anti-viral inhibitory RNA molecules to target cells.

BACKGROUND TO THE INVENTION

The application of gene therapy to the treatment of AIDS and HIV infection has been discussed widely (Lever, 1995). The types of therapeutic gene proposed usually fall into one of two broad categories. In the first the gene encodes protein products that inhibit the virus in a number of possible ways. One example of such a protein is the RevM10 derivative of the HIV Rev protein. The RevM10 protein acts as a transdominant negative mutant and so competitively inhibits Rev function in the virus. Like many of the protein-based strategies, the RevM10 protein is a derivative of a native HIV protein. While this provides the basis for the anti-HIV effect, it also has serious disadvantages. In particular, this type of strategy demands that in the absence of the virus there is little or no expression of the gene. Otherwise, healthy cells harbouring the gene become a target for the host cytotoxic T lymphocyte (CTL) system, which recognises the foreign protein. The second broad category of therapeutic gene circumvents these CTL problems. The therapeutic gene encodes inhibitory RNA molecules; RNA is not a target for CTL recognition.

There are several types of inhibitory RNA molecules known: anti-sense RNA, ribozyrnes, competitive decoys and external guide sequences (EGSs).

External guide sequences, first identified by Forster and Altman (1990), are RNA sequences that are capable of directing the cellular protein RNase P to cleave a particular RNA sequence. In vivo, they are found as part of precursor tRNAs where they function to direct cleavage by the cellular riboprotein RNase P in vivo of the tRNA precursor to form mature tRNA. However, in principle, any RNA can be targeted by a custom-designed EGS RNA for specific cleavage by RNase P in vitro or in viva. For example, Yuan et al. (1992) demonstrate a reduction in the levels of chloramphenicol activity in cells in tissue culture as a result of introducing an appropriately designed EGS.

In recent years a number of laboratories have developed retroviral vector systems based on HIV. In the context of anti-HIV gene therapy these vectors have a number of advantages over the more conventional murine based vectors such as murine leukaemia virus (MLV) vectors. Firstly, HIV vectors would target precisely those cells that are susceptible to HIV infection. Secondly, the HIV-based vector would transduce cells such as macrophages that are normally refractory to transduction by murine vectors. Thirdly, the anti-HIV vector genome would be propagated through the CD4+ cell population by any virus (HIV) that escaped the therapeutic strategy. This is because the vector genome has the packaging signal that will be recognised by the viral particle packaging system. These various attributes make HIV-vectors a powerful tool in the field of anti-HIV gene therapy.

A combination of inhibitory RNA molecules and an HIV-based vector would be attractive as a therapeutic strategy. However, until now this has not been possible. Vector particle production takes place in producer cells which express the packaging components of the particles and package the vector genome. The inhibitory RNA sequences that are designed to destroy the viral RNA would therefore also interrupt the expression of the components of the HIV-based vector system during vector production. The present invention aims to overcome this problem.

SUMMARY OF THE INVENTION

It is therefore an object of the invention to provide a system and method for producing viral particles, in particular HIV particles, which carry nucleotide constructs encoding inhibitory RNA molecules such as external guide sequences, optionally together with other classes of inhibitory RNA molecules such as ribozyrnes and/or antisense RNAs directed against a corresponding virus, such as HIV, within a target cell, that overcomes the above-mentioned problems. The system includes both a viral genome encoding the inhibitory RNA molcules and nucleotide constructs encoding the components required for packaging the viral genome in a producer cell. However, in contrast to the prior art, although the packaging components have substantially the same amino acid sequence as the corresponding components of the target virus, the inhibitory RNA molecules do not affect production of the viral particles in the producer cells because the nucleotide sequence of the packaging components used in the viral system have been modified to prevent the inhibitory RNA molecules from effecting cleavage or degradation of the RNA transcripts produced from the constructs. Such a viral particle may be used to treat viral infections, in particular HIV infections.

Accordingly the present invention provides a viral vector system comprising:

(i) a first nucleotide sequence encoding an external guide sequence capable of binding to and effecting the cleavage by RNase P of a second nucleotide sequence, or transcription product thereof, encoding a viral polypeptide required for the assembly of viral particles; and (ii) a third nucleotide sequence encoding said viral polypeptide required for the assembly of viral particles, which third nucleotide sequence has a different nucleotide sequence to the second nucleotide sequence such that the third nucleotide sequence, or transcription product thereof, is resistant to cleavage directed by the external guide sequence.

Preferably, said system further comprises at least one further first nucleotide sequence encoding a gene product capable of binding to and effecting the cleavage, directly or indirectly, of a second nucleotide sequence, or transcription product thereof, encoding a viral polypeptide required for the assembly of viral particles, wherein the gene product is selected from an external guide sequence, a ribozyme and an anti-sense ribonucleic acid.

In another aspect, the present invention provides a viral vector production system comprising:

(i) a viral genome comprising at least one first nucleotide sequence encoding a gene product capable of binding to and effecting the cleavage, directly or indirectly, of a second nucleotide sequence, or transcription product thereof, encoding a viral polypeptide required for the assembly of viral particles;

(ii) a third nucleotide sequence encoding said viral polypeptide required for the assembly of the viral genome into viral particles, which third nucleotide sequence has a different nucleotide sequence to the second nucleotide sequence such that said third nucleotide sequence, or transcription product thereof, is resistant to cleavage directed by said gene product;

wherein at least one of the gene products is an external guide sequence capable of binding to and effecting the cleavage by RNase P of the second nucleotide sequence.

Preferably, in addition to an external guide sequence, at least one gene product is selected from a ribozyme and an anti-sense ribonucleic acid, preferably a ribozyme.

Preferably, the viral vector is a retroviral vector, more preferably a lentiviral vector, such as an HIV vector. The second nucleotide sequence and the third nucleotide sequences are typically from the same viral species, more preferably from the same viral strain. Generally, the viral genome is also from the same viral species, more preferably from the same viral strain.

In the case of retroviral vectors, the polypeptide required for the assembly of viral particles is selected from gag, pol and env proteins. Preferably at least the gag and pol sequences are lentiviral sequences, more preferably HIV sequences. Alternatively, or in addition, the env sequence is a lentiviral sequence, more preferably an HIV sequence.

In a preferred embodiment, the third nucleotide sequence is resistant to cleavage directed by the gene product as a result of one or more conservative alterations in the nucleotide sequence which remove cleavage sites recognised by the at least one gene product and/or binding sites for the at least one gene product. For example, where the gene product is an EGS, the third nucleotide sequence is adapted to prevent EGS binding and/or to remove the RNase P consensus cleavage site. Alternatively, where the gene product is a ribozyme, the third nucleotide sequence is adapted to be resistant to cleavage by the ribozyme.

Preferably the third nucleotide sequence is codon optimised for expression in host cells. The host cells, which term includes producer cells and packaging cells, are typically mammalian cells.

In a particularly preferred embodiment, (i) the viral genome is an HIV genome comprising nucleotide sequences encoding anti-HIV EGSs and optionally anti-HIV ribozyme sequences directed against HIV packaging component sequences (such as gag.pol) in a target HIV and (ii) the viral system for producing packaged HIV particles further comprises nucleotide constructs encoding the same packaging components (such as gag.pol proteins) as in the target HIV wherein the sequence of the nucleotide constructs is different from that found in the target HIV so that the anti-HIV EGS and anti-HIV ribozyme sequences cannot effect cleavage or degradation of the gag.pol transcripts during production of the HIV particles in producer cells.

The present invention also provides a viral particle comprising a viral vector according to the present invention and one or more polypeptides encoded by the third nucleotide sequences according to the present invention. For example the present invention provides a viral particle produced using the viral vector production system of the invention.

In another aspect, the present invention provides a method for producing a viral particle which method comprises introducing into a host cell (i) a viral genome vector according to the present invention; (ii) one or more third nucleotide sequences according to the present invention; and (iii) nucleotide sequences encoding the other essential viral packaging components not encoded by the one or more third nucleotide sequences.

The present invention further provides a viral particle produced using by the method of the invention.

The present invention also provides a pharmaceutical composition comprising a viral particle according to the present invention together with a pharmaceutically acceptable carrier or diluent.

The viral system of the invention or viral particles of the invention may be used to treat viral infections, particularly retroviral infections such as lentiviral infections including HIV infections. Thus the present invention provides a method of treating a viral infection which method comprises administering to a human or animal patient suffering from the viral infection an effective amount of a viral system, viral particle or pharmaceutical composition of the present invention.

The invention relates in particular to HIV-based vectors carrying anti-HIV EGSs. However, the invention can be applied to any other virus, in particular any other lentivirus, for which treatment by gene therapy may be desirable. The invention is illustrated herein for HIV, but this is not considered to limit the scope of the invention to HIV-based anti-HIV vectors.

DETAILED DESCRIPTION OF THE INVENTION

The term "viral vector" refers to a nucleotide construct comprising a viral genome capable of being transcribed in a host cell, which genome comprises sufficient viral genetic information to allow packaging of the viral RNA genome, in the presence of packaging components, into a viral particle capable of infecting a target cell. Infection of the target cell includes reverse transcription and integration into the target cell genome, where appropriate for particular viruses. The viral vector in use typically carries heterologous coding sequences (nucleotides of interest) which are to be delivered by the vector to the target cell, for example a first nucleotide sequence encoding an EGS. A viral vector is incapable of independent replication to produce infectious viral particles within the final target cell.

The term "viral vector system" is intended to mean a kit of parts which can be used when combined with other necessary components for viral particle production to produce viral particles in host cells. For example, the first nucleotide sequence may typically be present in a plasmid vector construct suitable for cloning the first nucleotide sequence into a viral genome vector construct. When combined in a kit with a third nucleotide sequence, which will also typically be present in a separate plasmid vector construct, the resulting combination of plasmid containing the first nucleotide sequence and plasmid containing the third nucleotide sequence comprises the essential elements of the invention. Such a kit may then be used by the skilled person in the production of suitable viral vector genome constructs which when transfected into a host cell together with the plasmid containing the third nucleotide sequence, and optionally nucleic acid constructs encoding other components required for viral assembly, will lead to the production of infectious viral particles.

Alternatively, the third nucleotide sequence may be stably present within a packaging cell line that is included in the kit.

The kit may include the other components needed to produce viral particles, such as host cells and other plasmids encoding essential viral polypeptides required for viral assembly. By way of example, the kit may contain (i) a plasmid containing a first nucleotide sequence encoding an anti-HIV EGS and (ii) a plasmid containing a third nucleotide sequence encoding a modified HIV gag.pol construct which cannot be cleaved by the anti-HIV ribozyme. Optional components would then be (a) an HIV viral genome construct with suitable restriction enzyme recognition sites for cloning the first nucleotide sequence into the viral genome; (b) a plasmid encoding a VSV-G env protein. Alternatively, nucleotide sequence encoding viral polypeptides required for assembly of viral particles may be provided in the kit as packaging cell lines comprising the nucleotide sequences, for example a VSV-G expressing cell line.

The term "viral vector production system" refers to the viral vector system described above wherein the first nucleotide sequence has already been inserted into a suitable viral vector genome.

Viral vectors are typically retroviral vectors, in particular lentiviral vectors such as HIV vectors. The retroviral vector of the present invention may be derived from or may be derivable from any suitable retrovirus. A large number of different retroviruses have been identified. Examples include: murine leukemia virus (MLV), human immunodeficiency virus (HIV), simian immunodeficiency virus, human T-cell leukemia virus (HTLV). equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV). A detailed list of retroviruses may be found in Coffin et al., 1997, "Retroviruses", Cold Spring Harbour Laboratory Press Eds: J M Coffin, S M Hughes, H E Varmus pp 758-763.

Details on the genomic structure of some retroviruses may be found in the art. By way of example, details on HIV and Mo-MLV may be found from the NCBI Genbank (Genome Accession Nos. AF033819 and AF033811, respectively).

The lentivirus group can be split even further into "primate" and "non-primate". Examples of primate lentiviruses include human immunodeficiency virus (HIV), the causative agent of human auto-immunodeficiency syndrome (AIDS), and simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

The basic structure of a retrovirus genome is a 5' LTR and a 3' LTR, between or within which are located a packaging signal to enable the genome to be packaged, a primer binding site, integration sites to enable integration into a host cell genome and gag, pol and env genes encoding the packaging components—these are polypeptides required for the assembly of viral particles. More complex retroviruses have additional features, such as rev and RRE sequences in HIV, which enable the efficient export of RNA transcripts of the integrated provirus from the nucleus to the cytoplasm of an infected target cell.

In the provirus, these genes are flanked at both ends by regions called long terminal repeats (LTRs). The LTRs are responsible for proviral integration, and transcription. LTRs also serve as enhancer-promoter sequences and can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

In a defective retroviral vector genome gag, pol and env may be absent or not functional. The R regions at both ends of the RNA are repeated sequences. U5 and U3 represent unique sequences at the 5' and 3' ends of the RNA genome respectively.

In a typical retroviral vector for use in gene therapy, at least part of one or more of the gag, pol and env protein coding regions essential for replication may be removed from the virus. This makes the retroviral vector replication-defective. The removed portions may even be replaced by a nucleotide sequence of interest (NOI), such as a first nucleotide sequence of the invention, to generate a virus capable of integrating its genome into a host genome but wherein the modified viral genome is unable to propagate itself due to a lack of structural proteins. When integrated in the host genome, expression of the NOI occurs—resulting in, for example, a therapeutic and/or a diagnostic effect. Thus; the transfer of an NOI into a site of interest is typically achieved by: integrating the NOI into the recombinant viral vector; packaging the modified viral vector into a virion coat; and allowing transduction of a site of interest—such as a targeted cell or a targeted cell population.

A minimal retroviral genome for use in the present invention will therefore comprise (5') R—U5—one or more first nucleotide sequences—U3-R (3'). However, the plasmid vector used to produce the retroviral genome within a host cell/packaging cell will also include transcriptional regulatory control sequences operably linked to the retroviral genome to direct transcription of the genome in a host cell/packaging cell. These regulatory sequences may be the natural sequences associated with the transcribed retroviral sequence, i.e. the 5' U3 region, or they may be a heterologous promoter such as another viral promoter, for example the CMV promoter.

Some retroviral genomes require additional sequences for efficient virus production. For example, in the case of HIV, rev and RRE sequence are preferably included. However the requirement for rev and RRE can be reduced or eliminated by codon optimisation.

Once the retroviral vector genome is integrated into the genome of its target cell as proviral DNA, the ribozyme sequences need to be expressed. In a retrovirus, the promoter is located in the 5' LTR U3 region of the provirus. In retroviral vectors, the promoter driving expression of a therapeutic gene may be the native retroviral promoter in the 5' U3 region, or an alternative promoter engineered into the vector. The alternative promoter may physically replace the 5' U3 promoter native to the retrovirus, or it may be incorporated at a different place within the vector genome such as between the LTRs.

Thus, the first nucleotide sequence will also be operably linked to a transcriptional regulatory control sequence to allow transcription of the first nucleotide sequence to occur in the target cell. The control sequence will typically be active in mammalian cells. The control sequence may, for example, be a viral promoter such as the natural viral promoter or a CMV promoter or it may be a mammalian promoter. It is particularly preferred to use a promoter that is preferentially active in a particular cell type or tissue type in which the virus to be treated primarily infects. Thus, in one embodiment, a tissue-specific regulatory sequences may be used. The regulatory control sequences driving expression of the one or more first nucleotide sequences may be constitutive or regulated promoters.

Replication-defective retroviral vectors are typically propagated, for example to prepare suitable titres of the retroviral vector for subsequent transduction, by using a combination of a packaging or helper cell line and the recombinant vector. That is to say, that the three packaging proteins can be provided in trans.

A "packaging cell line" contains one or more of the retroviral gag, pol and env genes. The packaging cell line produces the proteins required for packaging retroviral DNA but it cannot bring about encapsidation due to the lack of a psi region. However, when a recombinant vector carrying an NOI and a psi region is introduced into the packaging cell line, the helper proteins can package the psi-positive recombinant vector to produce the recombinant virus stock. This virus stock can be used to transduce cells to introduce the NOI into the genome of the target cells. It is preferred to use a psi packaging signal, called psi plus, that contains additional sequences spanning from upstream of the splice donor to downstream of the gag start codon (Bender et al., 1987) since this has been shown to increase viral titres.

The recombinant virus whose genome lacks all genes required to make viral proteins can tranduce only once and cannot propagate. These viral vectors which are only capable of a single round of transduction of target cells are known as replication defective vectors.

Hence, the NOI is introduced into the host/target cell genome without the generation of potentially harmful retrovirus. A summary of the available packaging lines is presented in Coffin et al., 1997 (ibid).

Retroviral packaging cell lines in which the gag, pol and env viral coding regions are carried on separate expression plasmids that are independently transfected into a packaging cell line are preferably used. This strategy, sometimes referred to as the three plasmid transfection method (Soneoka et al., 1995) reduces the potential for production of a replication-competent virus since three recombinant events are required for wild type viral production. As recombination is greatly facilitated by homology, reducing or eliminating homology between the genomes of the vector and the helper can also be used to reduce the problem of replication-competent helper virus production.

An alternative to stably transfected packaging cell lines is to use transiently transfected cell lines. Transient transfections may advantageously be used to measure levels of vector production when vectors are being developed. In this regard, transient transfection avoids the longer time required to generate stable vector-producing cell lines and may also be used if the vector or retroviral packaging components are toxic to cells. Components typically used to generate retroviral vectors include a plasmid encoding the gag/pol proteins, a plasmid encoding the env protein and a plasmid containing an NOI. Vector production involves transient transfection of one or more of these components into cells containing the other required components. If the vector encodes toxic genes or genes that interfere with the replication of the host cell, such as inhibitors of the cell cycle or genes that induce apotosis, it may be difficult to generate stable vector-producing cell lines, but transient transfection can be used to produce the vector before the cells die. Also, cell lines have been developed using transient transfection that produce vector titre levels that are comparable to the levels obtained from stable vector-producing cell lines (Pear et al., 1993).

Producer cells/packaging cells can be of any suitable cell type. Most commonly, mammalian producer cells are used but other cells, such as insect cells are not excluded. Clearly, the producer cells will need to be capable of efficiently translating the env and gag, pol mRNA. Many suitable producer/packaging cell lines are known in the art. The skilled person is also capable of making suitable packaging cell lines by, for example stably introducing a nucleotide construct encoding a packaging component into a cell line.

As will be discussed below, where the retroviral genome encodes an inhibitory RNA molecule capable of effecting the cleavage of gag, pol and/or env RNA transcripts, the nucleotide sequences present in the packaging cell line, either integrated or carried on plasmids, or in the transiently transfected producer cell line, which encode gag, pol and or env proteins will be modified so as to reduce or prevent binding of the inhibitory RNA molecule(s). In this way, the inhibitory RNA molecule(s) will not prevent expression of components in packaging cell lines that are essential for packaging of viral particles.

It is highly desirable to use high-titre virus preparations in both experimental and practical applications. Techniques for increasing viral titre include using a psi plus packaging signal as discussed above and concentration of viral stocks. In addition, the use of different envelope proteins, such as the G protein from vesicular-stomatitis virus has improved titres following concentration to $10^9$ per ml (Cosset et al., 1995). However, typically the envelope protein will be chosen such that the viral particle will preferentially infect cells that are infected with the virus which it desired to treat. For example where an HIV vector is being used to treat HIV infection, the env protein used will be the HIV env protein.

Suitable first nucleotide sequences for use according to the present invention encode gene products that result in the cleavage and/or enzymatic degradation of a target nucleotide sequence, which will generally be a ribonucleotide. As particular examples, EGSs, ribozymes, and antisense sequences may be mentioned, more specifically EGSs.

External guide sequences (EGSs) are RNA sequences that bind to a complementary target sequence to form a loop in the target RNA sequence, the overall structure being a substrate for RNaseP-mediated cleavage of the target RNA sequence. The structure that forms when the EGS anneals to the target RNA is very similar to that found in a tRNA precursor. The the natural activity of RNaseP can be directed to cleave a target RNA by designing a suitable EGS. The general rules for EGS design are as follows, with reference to the generic EGSs shown in FIG. 9B:

Rules for EGS Design in Mammalian Cells (See FIG. 9B)

Target sequence—All tRNA precursor molecules have a G immediately 3' of the RNaseP cleavage site (i.e. the G forms a base pair with the C at the top of the acceptor stem prior to the ACCA sequence). In addition a U is found 8 nucleotides downstream in all tRNAs. (i.e. G at position 1, U at position 8). A pyrimidine may be preferred 5' of the cut site. No other specific target sequences are required.

EGS sequence—A 7 nucleotide 'acceptor stem' analogue is optimal (5' hybridising arm). A 4 nucleotide 'D-stem' analogue is preferred (3' hybridising arm). Variation in this length may alter the reaction kinetics. This will be specific to each target site. A consensus 'T-stem and loop' analogue is essential. Minimal 5' and 3' non-pairing sequences are preferred to reduce the potential for undesired folding of the EGS RNA.

Deletion of the 'anti-codon stem and loop' analogue may be beneficial. Deletion of the variable loop can also be tolerated in vitro but an optimal replacement loop for the deletion of both has not been defined in vivo.

As with ribozymes, described below, it is preferred to use more than one EGS. Preferably, a plurality of EGSs is employed, together capable of cleaving gag, pol and env RNA of the native retrovirus at a plurality of sites. Since HIV exists as a population of quasispecies, not all of the target sequences for the EGSs will be included in all HIV variants. The problem presented by this variability can be overcome by using multiple EGs. Multiple EGSs can be included in series in a single vector and can function independently when expressed as a single RNA sequence. A single RNA containing two or more EGSs having different target recognition sites may be referred to as a multitarget EGS.

Further guidance may be obtained by reference to, for example, Werner et al. (1997); Werner et al. (1998); Ma et al. (1998) and Kawa et al. (1998).

Ribozymes are RNA enzymes which cleave RNA at specific sites. Ribozymes can be engineered so as to be specific for any chosen sequence containing a ribozyme cleavage site. Thus, ribozymes can be engineered which have chosen recognition sites in transcribed viral sequences. By way of an example, ribozymes encoded by the first nucleotide sequence recognise and cleave essential elements of viral genomes required for the production of viral particles, such as packaging components. Thus, for retroviral genomes, such essential elements include the gag, pod and env gene products. A suitable ribozyme capable of recognising at least one of the gag, pol and env gene sequences, or more typically, the RNA sequences transcribed from these genes, is able to bind to and cleave such a sequence. This will reduce or prevent production of the gal, pol or env protein as appropriate and thus reduce or prevent the production of retroviral particles.

Ribozymes come in several forms, including hammerhead, hairpin and hepatitis delta antigenomic ribozymes. Preferred for use herein are hammerhead ribozymes, in part because of their relatively small size, because the sequence requirements for their target cleavage site are minimal and because they have been well characterised. The ribozymes most commonly used in research at present are hammerhead and hairpin ribozymes.

Each individual ribozyme has a motif which recognises and binds to a recognition site in the target RNA. This motif takes the form of one or more "binding arms", generally two binding arms. The binding arms in hammerhead ribozymes are the flanking sequences Helix I and Helix III, which flank Helix II. These can be of variable length, usually between 6 to 10 nucleotides each, but can be shorter or longer. The length of the flanking sequences can affect the rate of cleavage. For example, it has been found that reducing the total number of nucleotides in the flanking sequences from 20 to 12 can increase the turnover rate of the ribozyme cleaving a HIV sequence, by 10-fold (Goodchild et al., 1991). A catalytic motif in the ribozyme Helix II in hammerhead ribozymes cleaves the target RNA at a site which is referred to as the cleavage site. Whether or not a ribozyme will cleave any given RNA is determined by the presence or absence of a recognition site for the ribozyme containing an appropriate cleavage site.

Each type of ribozyme recognises its own cleavage site. The hammerhead ribozyme cleavage site has the nucleotide base triplet GUX directly upstream where G is guanine, U is uracil and X is any nucleotide base. Hairpin ribozymes have a cleavage site of BCUGNYR, where B is any nucleotide base other than adenine, N is any nucleotide, Y is cytosine or thymine and R is guanine or adenine. Cleavage by hairpin ribozymes takes places between the G and the N in the cleavage site.

The nucleic acid sequences encoding the packaging components (the "third nucleotide sequences") may be resistant to the ribozyme or ribozymes because they lack any cleavage sites for the ribozyme or ribozymes. This prohibits enzymatic activity by the ribozyme or ribozymes and therefore there is no effective recognition site for the ribozyme or ribozymes. Alternatively or additionally, the potential recognition sites may be altered in the flanking sequences which form the part of the recognition site to which the ribozyme binds. This either eliminates binding of the ribozyme motif to the recognition site, or reduces binding capability enough to destabilise any ribozyme-target complex and thus reduce the specificity and catalytic activity of the ribozyme. Where the flanking sequences only are altered, they are preferably altered such that catalytic activity of the ribozyme at the altered target sequence is negligible and is effectively eliminated.

Preferably, a series of several anti-HIV ribozymes is employed in the invention. These can be any anti-HIV ribozymes but must include one or more which cleave the RNA that is required for the expression of gag, pot or env. Preferably, a plurality of ribozymes is employed, together capable of cleaving gag, pot and env RNA of the native retrovirus at a plurality of sites. Since HIV exists as a population of quasispecies, not all of the target sequences for the ribozymes will be included in all HIV variants. The problem presented by this variability can be overcome by using multiple ribozymes. Multiple ribozymes can be included in series in a single vector and can function independently when expressed as a single RNA sequence. A single RNA containing two or more ribozymes having different target recognition sites may be referred to as a multitarget ribozyme. The placement of ribozymes in series has been demonstrated to enhance cleavage. The use of a plurality of ribozymes is not limited to treating HIV infection but may be used in relation to other viruses, retroviruses or otherwise.

Antisense technology is well known on the art. There are various mechanisms by which antisense sequences are believed to inhibit gene expression. One mechanism by which antisense sequences are believed to function is the recruitment of the cellular protein RNaseH to the target sequence/antisense construct heteroduplex which results in cleavage and degradation of the heteroduplex. Thus the antisense construct, by contrast to ribozymes, can be said to lead indirectly to cleavage/degradation of the target sequence. Thus according to the present invention, a first nucleotide sequence may encode an antisense RNA that binds to either a gene encoding an essential/packaging component or the RNA transcribed from said gene such that expression of the gene is inhibited, for example as a result of RNaseH degradation of a resulting heteroduplex. It is not necessary for the antisense construct to encode the entire complementary sequence of the gene encoding an essential/packaging component—a portion may suffice. The skilled person will easily be able to determine how to design a suitable antisense construct.

By contrast, the nucleic acid sequences encoding the essential/packaging components of the viral particles required for the assembly of viral particles in the host cells/producer cells/packaging cells (the third nucleotide sequences) are resistant to the inhibitory RNA molecules encoded by the first nucleotide sequence. For example in the case of ribozymes, resistance is typically by virtue of alterations in the sequences which eliminate the ribozyme recognition sites. At the same time, the amino acid coding sequence for the essential/packaging components is retained so that the viral components encoded by the sequences remain the same, or at least sufficiently similar that the function of the essential/packaging components is not compromised.

The term "viral polypeptide required for the assembly of viral particles" means a polypeptide normally encoded by the viral genome to be packaged into viral particles, in the absence of which the viral genome cannot be packaged. For example, in the context of retroviruses such polypeptides would include gag, pol and env. The terms "packaging component" and "essential component" are also included within this definition.

In the case of antisense sequences, the third nucleotide sequence differs from the second nucleotide sequence encoding the target viral packaging component antisense sequence to the extent that although the antisense sequence can bind to the second nucleotide sequence, or transcript thereof, the antisense sequence can not bind effectively to the third nucleotide sequence or RNA transcribed from therefrom The changes between the second and third nucleotide sequences will typically be conservative changes, although a small number of amino acid changes may be tolerated provided that, as described above, the function of the essential/packaging components is not significantly impaired.

Preferably, in addition to eliminating the inhibitory RNA recognition sites, the alterations to the coding sequences for the viral components improve the sequences for codon usage in the mammalian cells or other cells which are to act as the producer cells for retroviral vector particle production. This improvement in codon usage is referred to as "codon optimisation". Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Thus preferably, the sequences encoding the packaging components are codon optimised. More preferably, the sequences are codon optimised in their entirety. Following codon optimisation, it is found that there are numerous sites in the wild type gag, pol and env sequences which can serve as inhibitory RNA recognition sites and which are no longer present in the sequences encoding the packaging components. In an alternative but less practical strategy, the sequences encoding the packaging components can be altered by targeted conservative alterations so as to render them resistant to selected inhibitory RNAs capable of effecting the cleavage of the wild type sequences.

An additional advantage of codon optimising HIV packaging components is that this can increase gene expression. In particular, it can render gag, pol expression Rev independent so that rev and RRE need not be included in the genome (Haas et at., 1996). Rev-independent vectors are therefore possible. This in turn enables the use of anti-rev or RRE factors in the retroviral vector.

As described above, the packaging components for a retroviral vector include expression products of gag, pol and env genes. In accordance with the present invention, gag and pol employed in the packaging system are derived from the target retrovirus on which the vector genome is based. Thus, in the RNA transcript form, gag and pol would normally be cleavable by the ribozymes present in the vector genome. The env gene employed in the packaging system may be derived from a different virus, including other retroviruses such as MLV and non-retroviruses such as VSV (a Rhabdovirus), in which case it may not need any sequence alteration to render it resistant to cleavage effected by the inhibitory RNA(s). Alternatively, env may be derived from the same retrovirus as gag and pol, in which case any recognition sites for the inhibitory RNA(s) will need to be eliminated by sequence alteration.

The process of producing a retroviral vector in which the envelope protein is not the native envelope of the retrovirus is known as "pseudotyping". Certain envelope proteins, such as MLV envelope protein and vesicular stomatitis virus G (VSV-G) protein, pseudotype retroviruses very weft. Pseudotyping can be useful for altering the target cell range of the retrovirus. Alternatively, to maintain target cell specificity for target cells infected with the a particular virus it is desired to treat, the envelope protein may be the same as that of the target virus, for example HIV.

Other therapeutic coding sequences may be present along with the first nucleotide sequence or sequences. Other therapeutic coding sequences include, but are not limited to, sequences encoding cytokines, hormones, antibodies, immunoglobulin fusion proteins, enzymes, immune co-stimulatory molecules, anti-sense RNA, a transdominant negative mutant of a target protein, a toxin, a conditional toxin, an antigen, a single chain antibody, tumour suppresser protein and growth factors. When included, such coding sequences are operatively linked to a suitable promoter, which may be the promoter driving expression of the first nucleotide sequence or a different promoter or promoters.

Thus the invention comprises two components. The first is a genome construction that will be packaged by viral packaging components and which carries a series of anti-viral inhibitory RNA molecules such as anti-HIVEGs. These could be any anti-HIV EGSs but the key issue for this invention is that some of them result in cleavage of RNA that is required for the expression of native or wild type HIV gag, pol or env coding sequences. The second component is the packaging system which comprises a cassette for the expression of HIV gag, pol and a cassette either for HIV env or an envelope gene encoding a pseudotyping envelope protein—the packaging system being resistant to the inhibitory RNA molecules.

The viral particles of the present invention, and the viral vector system and methods used to produce may thus be used to treat or prevent viral infections, preferably retroviral infections, in particular lentiviral, especially HIV, infections. Specifically, the viral particles of the invention, typically produced using the viral vector system of the present invention may be used to deliver inhibitory RNA molecules to a human or animal in need of treatment for a viral infection.

Alternatively, or in addition, the viral production system may be used to transfect cells obtained from a patient ex vivo and then returned to the patient. Patient cells transfected ex vivo may be formulated as a pharmaceutical composition (see below) prior to readministration to the patient.

Preferably the viral particles are combined with a pharmaceutically acceptable carrier or diluent to produce a pharmaceutical composition. Thus, the present invention also provides a pharmaceutical composition for treating an individual, wherein the composition comprises a therapeutically effective amount of the viral particle of the present invention, together with a pharmaceutically acceptable carrier, diluent, excipient or adjuvant. The pharmaceutical composition may be for human or animal usage.

The choice of pharmaceutical carrier, excipient or diluent can be selected with regard to the intended route of administration and standard pharmaceutical practice. Suitable carriers and diluents include isotonic saline solutions, for example phosphate-buffered saline. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system).

The pharmaceutical composition may be formulated for parenteral, intramuscular, intravenous, intracranial, subcutaneous, oral, intraocular or transdermal administration.

Where appropriate, the pharmaceutical compositions can be administered by any one or more of inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The amount of virus administered is typically in the range of from $10^3$ to $10^{10}$ pfu, preferably from $10^5$ to $10^8$ pfu, more preferably from $10^6$ to $10^7$ pfu. When injected, typically 1–10 μl of virus in a pharmaceutically acceptable suitable carrier or diluent is administered.

When the polynucleotide/vector is administered as a naked nucleic acid, the amount of nucleic acid administered is typically in the range of from 1 μg to 10 mg, preferably from 100 μg to 1 mg.

Where the first nucleotide sequence (or other therapeutic sequence) is under the control of an inducible regulatory sequence, it may only be necessary to induce gene expression for the duration of the treatment. Once the condition has been treated, the inducer is removed and expression of the NOT is stopped. This will clearly have clinical advantages. Such a system may, for example, involve administering the antibiotic tetracycline, to activate gene expression via its effect on the tet repressor/VP16 fusion protein.

The invention will now be further described by way of Examples, which are meant to serve to assist one of ordinary skill in the art in carrying out the invention and are not intended in any way to limit the scope of the invention. The Examples refer to the Figures. In the Figures:

FIG. 1 shows schematically ribozyrnes inserted into four different HIV vectors;

FIG. 2 shows schematically how to create a suitable 3' LTR by PCR;

FIG. 3 shows the codon usage table for wild type HIV gag,pol of strain HXB2 (accession number: K03455).

FIG. 4 shows the codon usage table of the codon optimised sequence designated gag,pol-SYNgp.

FIG. 5 shows the codon usage table of the wild type HIV env called env-mn.

FIG. 6 shows the codon usage table of the codon optimised sequence of HIV env designated SYNgp160 mn

FIG. 8 shows the principle behind two systems for producing retroviral vector particles.

Figure 7:
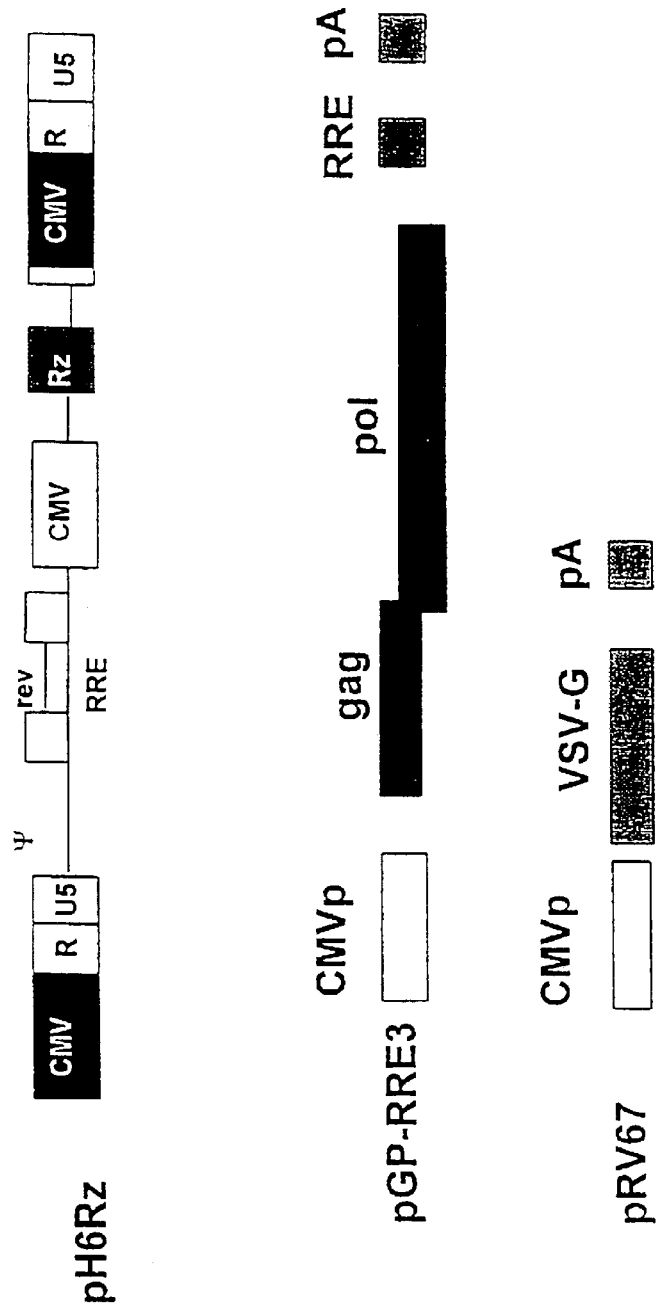
FIG. 7 shows three plasmid constructs for use in the invention.
Figure 9:
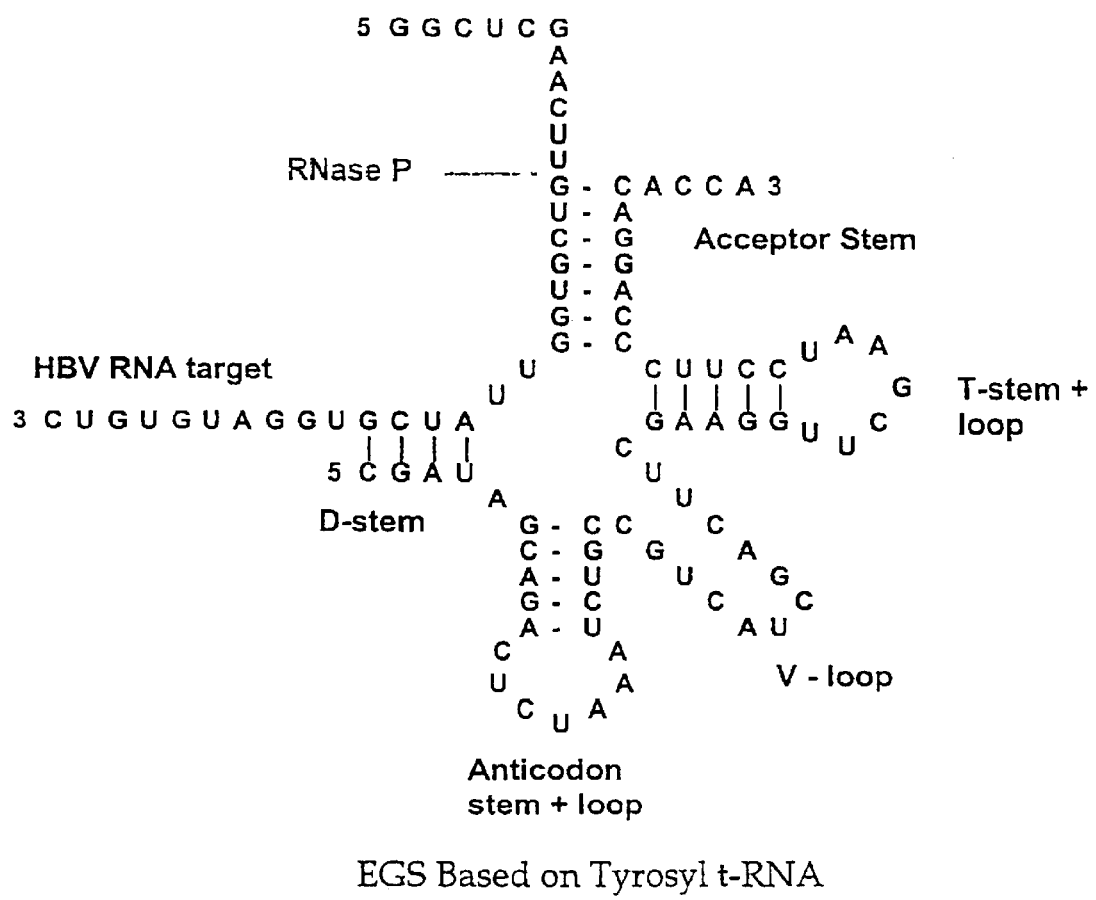
FIG. 9A shows an EGS based on tyrosyl t-RNA
FIG. 9B shows a consensus EGS sequence.
Figure 9:
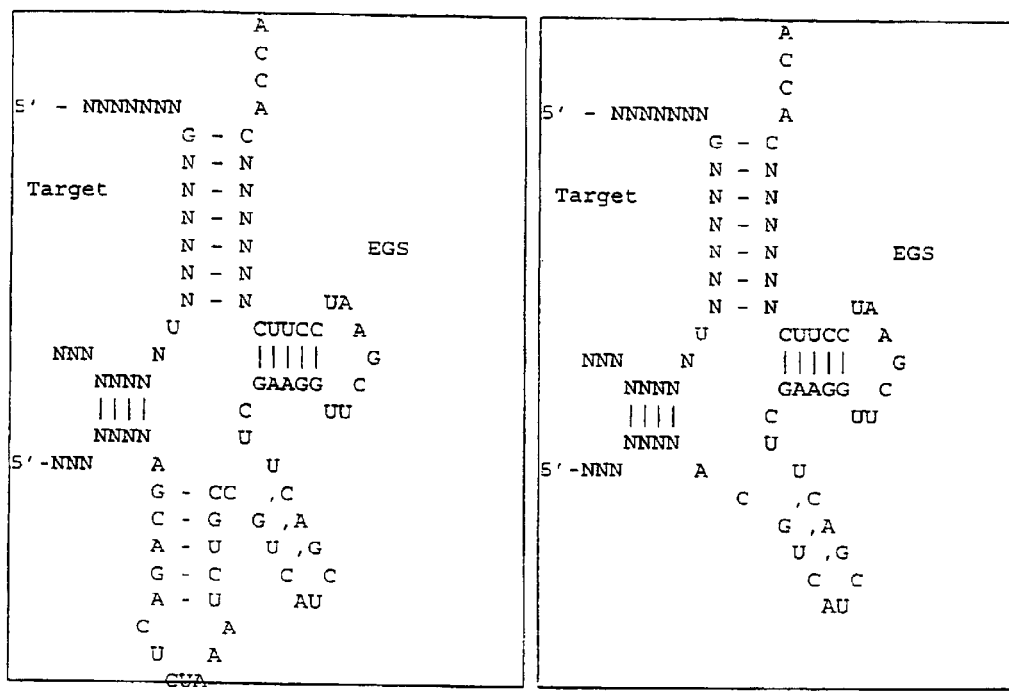
Figure 10:
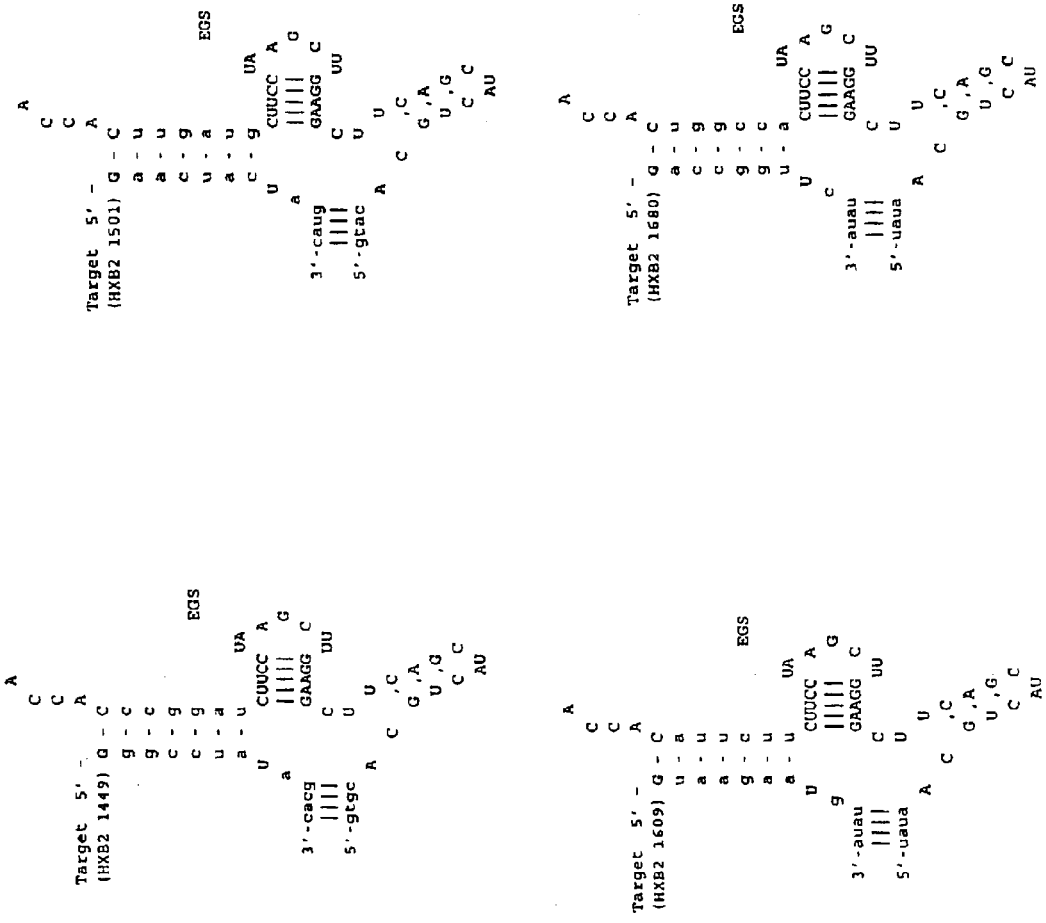
FIG. 10 shows twelve different anti-HIV EGS constructs.
Figure 10:
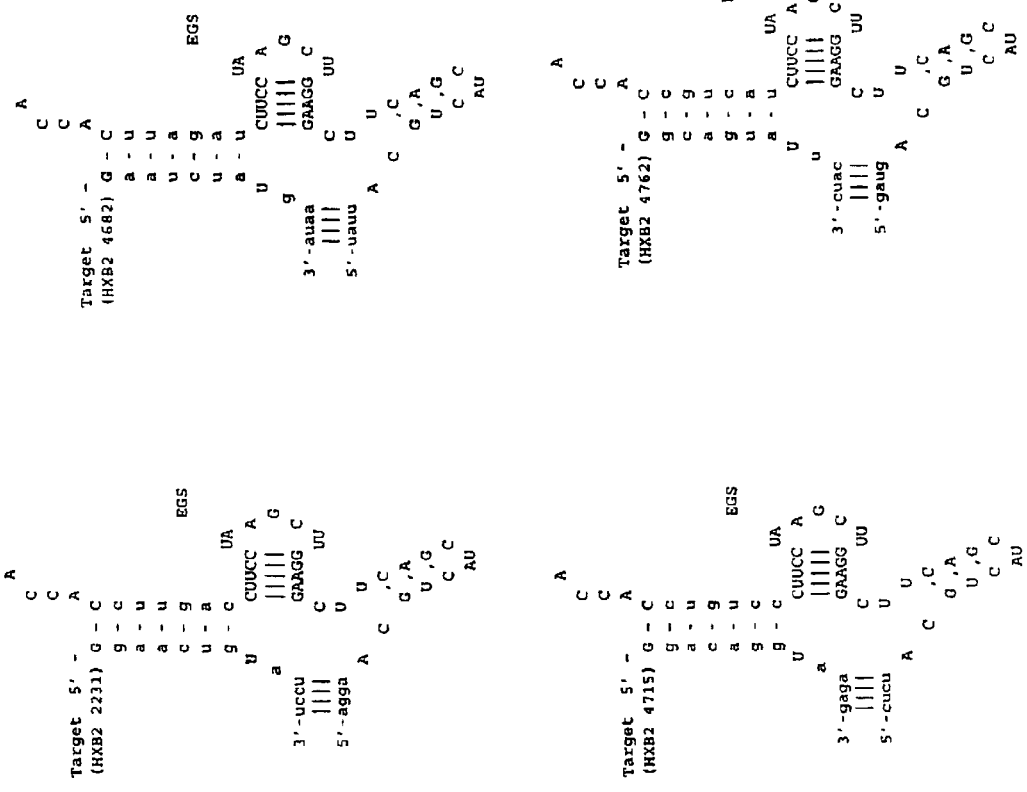

The invention will now be further described in the Examples which follow, which are intended as an illustration only and do not limit the scope of the invention.

EXAMPLES

Reference Example 1—Construction of a Ribozyme-encoding Genome

The HIV gag.pol sequence was codon optimised (FIG. 4 and SEQ I.D. No. 1) and synthesised using overlapping oligos of around 40 nucleotides. This has three advantages. Firstly it allows an HIV based vector to carry ribozymes and other therapeutic factors. Secondly the codon optimisation generates a higher vector titre due to a higher level of gene expression. Thirdly gag.pol expression becomes rev independent which allows the use of anti-rev or RRE factors.

Conserved sequences within gag.pol were identified by reference to the HIV Sequence database at Los Alamos National Laboratory (http:// hiv-web.lanl.gov/) and used to design ribozymes. Because of the variability between subtypes of HIV-1 the ribozymes were designed to cleave the predominant subtype within North America, Latin America and the Caribbean, Europe, Japan and Australia; that is subtype B. The sites chosen were cross-referenced with the synthetic gagpol sequence to ensure that there was a low possibility of cutting the codon optimised gagpol mRNA. The ribozyrnes were designed with XhoI and SalI sites at the 5' and 3' end respectively. This allows the construction of separate and tandem ribozymes.

The ribozymes are hammerhead (Riddell et al., 1996) structures of the following general structure:

```
                                              (SEQ ID NO: 15)
Helix I            Helix II            Helix III
5'-NNNNNNNN~    CUGAUGAGGCCGAAAGGCCGAA    ~NNNNNNNN~
```

The catalytic domain of the ribozyme (Helix II) can tolerate some changes without reducing catalytic turnover.

The cleavage sites, targeting gag and pol with the essential GUX triplet (where X is any nucleotide base) are as follows:

GAG 1 5' UAGUAAGAAUGUAUAGCCCUAC (SEQ ID NO: 16)

GAG 2 5' AACCCAGAUUGUAAGACUAUUU (SEQ ID NO: 17)

GAG 3 5' UGUUUCAAUUGUGGCAAAGAAG (SEQ ID NO: 18)

GAG 4 5' AAAAAGGGCUGUUGGAAAUGUG (SEQ ID NO: 19)

POL 1 5' ACGACCCCUCGUCACAAUAAAG (SEQ ID NO: 20)

POL 2 5' GGAAUUGGAGGUUUUAUCAAAG (SEQ ID NO: 21)

POL 3 5' AUAUUUUUCAGUUCCCUUAGAU (SEQ ID NO. 22)

POL 4 5' UGGAUGAUUUGUAUGUAGGAUC (SEQ ID NO: 23)

POL 5 5° CUUUGGAUGGGUUAUGAACUCC (SEQ ID NO: 24)

POL 6 5° CAGCUGGACUGUCAAUGACAUA (SEQ ID NO: 25)

POL 7 5' AACUUUCUAUGUAGAUGGGGCA (SEQ ID NO: 26)

POL 8 5' AAGGCCGCCUGUUGGUGGGCAG (SEQ ID NO: 27)

POL 9 5' UAAGACAGCAGUACAAAUGGCA (SEQ ID NO: 28)

The ribozymes are inserted into four different HIV vectors (pH4 (Gervaix et al., 1997), pH6, pH4.1, or pH6.1) (FIG. 1). In pH4 and pH6, transcription of the ribozymes is driven by an internal HCMV promoter (Foecking et al., 1986). From pH4.1 and pH6.1, the ribozymes are expressed from the 5' LTR. The major difference between pH4 and pH6 (and pH4.1 and pH6.1) resides in the 3' LTR in the production plasmid. pH4 and pH4.1 have the HIV U3 in the 3' LTR. pH6 and pH6.1 have HCMV in the 3'LTR. The HCMV promoter replaces most of the U3 and will drive expression at high constitutive levels while the HIV-1 U3 will support a high level of expression only in the presence of Tat.

The HCMV/HIV-1 hybrid 3' LTR is created by recombinant PCR with three PCR primers (FIG, 2), The first round of PCR is performed with RIB1 and RIB2 using pH4 (Kim et al., 1998) as the template to amplify the HIV-1 HXB2 sequence 8900–9123. The second round of PCR makes the junction between the 4' end of the HIV-1 U3 and the HCMV promoter by amplifying the hybrid 5' LTR from pH4. The PCR product from the first PCR reaction and RIB3 serves as the 5' primer and 3' primer respectively.

RIB1: 5' CAGCTGCTCGAGCAGCTGAAGCTTG-CATGC 3' (SEQ ID NO: 29)

RIB2: 5' GTAAGTTATGTAACGGACGATATCT-TGTCTTCTT 3' (SEQ ID NO: 30)

RIB3: 5' CGCATAGTCGACGGGCCCGCCACTGCTA-GAGATTTTC 3' (SEQ ID NO: 31)

The PCR product is then cut with SphI and SalI and inserted into pH4 thereby replacing the 3' LTR. The resulting plasmid is designated pH6. To construct pH4.1 and pH6.1, the internal HCMV promoter (SpeI-XhoI) in pH4 and pH6 is replaced with the polycloning site of pBluescript II KS+ (Stratagene) (SpeI-XhoI).

The ribozymes are inserted into the XhoI sites in the genome vector backbones. Any ribozymes in any configuration could be used in a similar way.

Reference Example 2—Construction of a Packaging System

The packaging system can take various forms. In a first form of packaging system, the HIV gag, pol components are co-expressed with the HIV env coding sequence. In this case, both the gag, pol and the env coding sequences are altered such that they are resistant to the anti-HIV ribozymes that are built into the genome. At the same time as altering the codon usage to achieve resistance, the codons can be chosen to match the usage pattern of the most highly expressed mammalian genes. This dramatically increases expression levels and so increases titre. A codon optimised HIV env coding sequence has been described by Haas et al. (1996). In the present example, a modified codon optimised HIV env sequence is used (SEQ I.D. No. 3). The corresponding env expression plasmid is designated pSYNgp 160 mn. The modified sequence contains extra motifs not used by Haas et at. The extra sequences were taken from the HIV env sequence of strain MN and codon optimised. Any similar modification of the nucleic acid sequence would function similarly as long as it used codons corresponding to abundant tRNAs (Zolotukhin et al., 1996) and lead to resistance to the ribozymes in the genome.

In one example of a gag, pol coding sequence with optimised codon usage, overlapping oligonucleotides are synthesised and then ligated together to produce the synthetic coding sequence. The sequence of a wild-type (Genbank accession no. K03455) and synthetic (gagpol-SYNgp) gagpol sequence is shown in SEQ I.D. Nos 1 and 2, respectively and their codon usage is shown in FIGS. 3 and 4, respectively. The sequence of a wild type env coding sequence (Genbank Accession No. M17449) is given in SEQ I.D. No 3, the sequence of a synthetic codon optimised sequence is given in SEQ. I.D. No. 4 and their codon usage tables are given in FIGS. 5 and 6, respectively. As with the env coding sequence any gag, pol sequence that achieves resistance to the ribozymes could be used. The synthetic sequence shown is designated gag, pol-SYNgp and has an EcoRI site at the 5' end and a NotI site at the 3' end. It is inserted into pClneo (Promega) to produce plasmid pSYNgp.

The sequence of the codon optimised gagpol sequence is shown in SEQ I.D. No. 2. This sequence starts at the ATG and ends at the stop codon of gagpol. The wild type sequence is retained around the frameshift site so that the right amount of gagpol is made.

In addition other constructs can be used that contain the optimised gagpol of pSYNgp but also have differing amounts of the wild type HIV 1 sequence of strain HXB2 (accession number: K03455) at the 5' end. These constructs are described below (the start ATG of pSYNgp is shown in bold in these sequences).

pSYNgp2 contains the entire leader sequence of HIV-1 (SEQ ID. No. 12).

pSYNgp3 contains the leader sequence of HIV-1 from the major splice donor (SEQ ID. No. 13).

pSYNgp4 contains 20 pb of the leader sequence of HIV-1 upstream of the start codon of ATG (SEQ ID. No. 14).

These constructs may be made by overlapping PCR. Using appropriate restriction enzymes these sequences can be inserted into mammalian expression vectors such as pCI-Neo (Promega). All these gag/pol constructs can be used to supply HIV gag/pol for the generation of viral vectors. These viral vectors can be used to express either EGS molecules or ribozyme molecules or antisense molecules or any peptides or proteins.

In a second form of the packaging system a synthetic gag, pol cassette is coexpressed with a non-HIV envelope coding sequence that produces a surface protein that pseudotypes HIV. This could be for example VSV-G (Ory et al., 1996; Zhu et al 1990), amphotropic MLV env (Chesebro et al., 1990; Spector et al., 1990) or any other protein that would be incorporated into the HIV particle (Valsesia-Wittnan, 1994). This includes molecules capable of targeting the vector to specific tissues. Coding sequences for non-HIV envelope proteins not cleaved by the ribozymes and so no sequence modification is required (although some sequence modification may be desirable for other reasons such as optimisation for codon usage in mammalian cells).

Reference Example 3—Vector Particle Production

Vector particles can be produced either from a transient three-plasmid transfection system similar to that described by Soneoka et al. (1995) or from producer cell lines similar to those used for other retroviral vectors (Ory et al., 1996;

Srinivasakumar et al., 1997; Yu et al., 1996). These principles are illustrated in FIGS. 7 and 8. For example, by using pH6Rz, pSYNgp and pRV67 (VSV-G expression plasmid) in a three plasmid transfection of 293T cells (FIG. 8), as described by Soneoka et at. (1995), vector particles designated H6Rz-VSV are produced. These transduce the H6Rz genome to CD4+ cells such as C1866 or Jurkat and produce the multitarget ribozymes. HIV replication in these cells is now severely restricted.

Example 1—Use of External Guide Sequences for Inhibiting HIV

Ribonuclease P is a nuclear localised enzyme consisting of protein and RNA subunits. It has been found in all organisms examined and is one of the most abundant, stable and efficient enzymes in cells. Its enzymatic activity is responsible for the maturation of the 5' termini of all tRNAs which account for about 2% of the total cellular RNA.

For tRNA processing, it has been shown that RNAse P recognises a secondary structure of the tRNA. However extensive studies have shown that any complex of two RNA molecules which resemble the one tRNA molecule will also be recognised and cleaved by RNase P. Consequently the natural activity of RNase P can and has been successfully re-directed to target other RNA species (see Yaun and Altman, 1994, and references therein). This is achieved by engineering a sequence, containing the flanking motif recognised by RNaseP, to bind the desired target sequence. These sequences are called external guide sequence (EGSs).

Outlined here is a strategy employing the EGS system against HIV RNA. Shown in FIG. 2A, B and C are twelve EGS sequences designed to target twelve separate HIV gag/pol sequences. These target sequences are conserved throughout the clade B of HIV. The sequence numbering in each figure designates the position of the required conserved G of each target sequences based on the HXB2 published sequence.

The external guide sequences shown here all have anticodon stem-loops deleted. These are non-limiting examples; for instance full length 3/4 tRNA based EGSs might be used if preferred (see Yuan and Altman, 1994).

Figure 11:
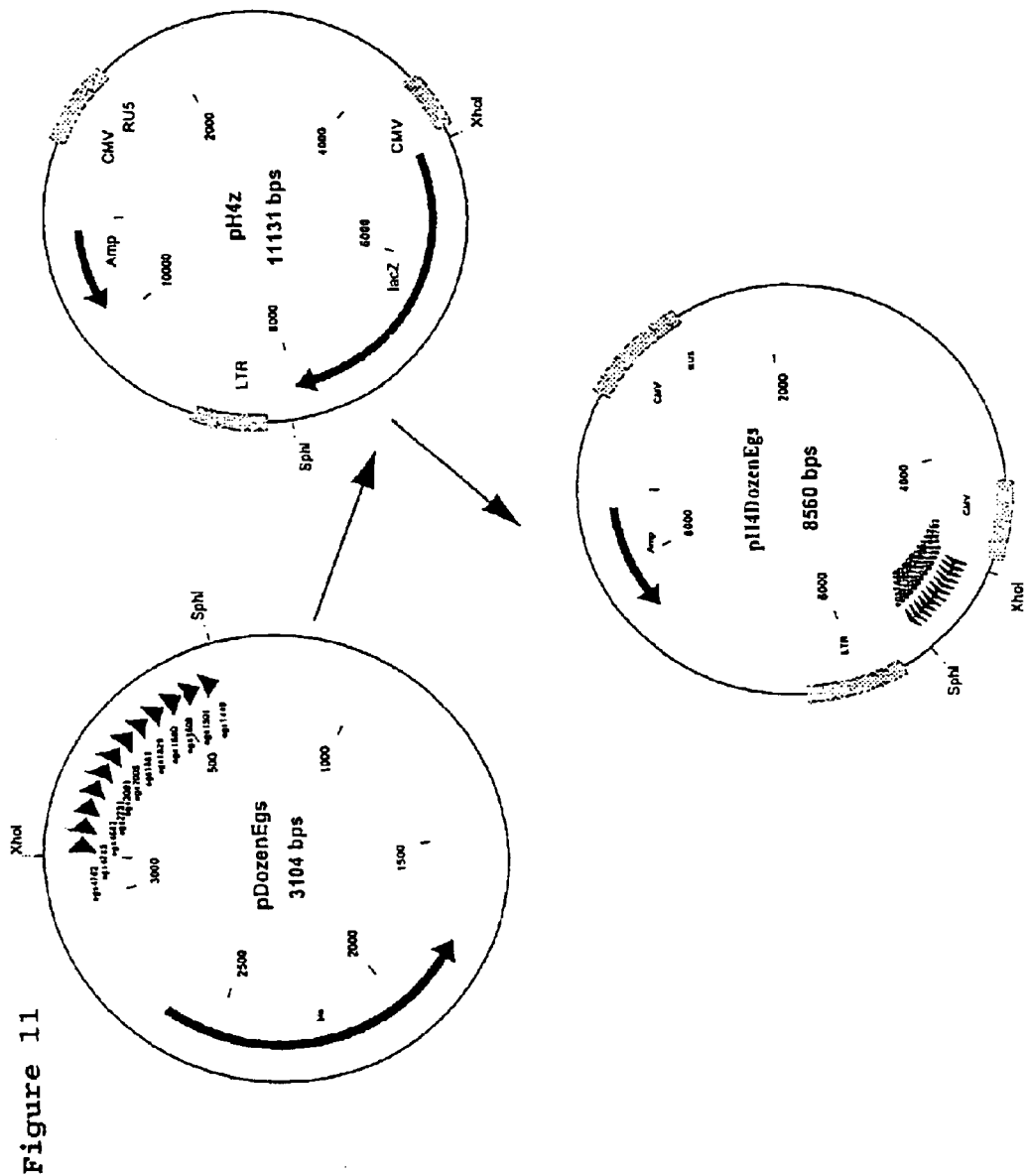
FIG. 11 is a schematic representation of pDozenEgs and construction of pH4DozenEgs.

Outlined in SEQ ID. Nos. 5 to 10 (see below) and FIG. 11 is the cloning strategy employed to construct an HIV vector containing the EGSs described in SEQ ID. Nos. 5 to 10. The oligonucleotides prefixed 1, 2, 3, 4, 5 and 6 are respectively annealed together and sequentially cloned into the pSP72 (Promega) cloning vector starting with the oligo. duplex 1/1A being cloned into the XhoI-SalI site such that the EGS 4762 and EGS 4715 are orientated away from the ampicillin gene. The remaining oligonucleotides (with XhoI ends) are subsequently cloned stepwise (starting with oligo. duplex 2/2A, ending with duplex 6/6A) into the unique SalI site (present within the terminus of the each preceding oligonucleotide) to create the plasmid pDOZENEGS. The EGSs from this vector are then transferred by XhoI-SphI digest into the pH4Z similarily cut such that the multiple EGSs cassette replaces the lacZ gene of pH4Z (Kim et al., 1998). The resulting vector is named pH4DOZENEGS (see SEQ ID. No. 11 for complete sequence).

Egs 1/1A (SEQ ID NO. 5)

(SEQ ID NO: 5) 5'-tcgagcccggggatgacgtcatcgacttcgaaggttcgaatccttctactgccaccattttttt cgggccctactgcagtagctgaagcttccaagcttaggaagatgacggtggtaaaaaa ctctacgtcatcgacttcgaaggttcgaatccttccctgtccaccagtcgacc-3' gagatgcagtagctgaagcttccaagcttaggaagggacaggtggtcagctggagct-5' SEQ ID NO: 32)

Egs 2/2A (SEQ ID NO. 6)

(SEQ ID NO. 6) 5'-tcgagtattacgtcatcgacttcgaaggttcgaatccttctagattcaccattttttaggaacg cataatgcagtagctgaagcttccaagcttaggaagtactaagtggtaaaaaatccttgc tcatcgacttcg aaggttcgaatccttccagttccaccagtcgacc-3' agtagctgaagcttccaagcttaggaaggtcaaggtggtcagctggagct-5' (SEQ ID NO. 33)

Egs 3/3A (SEQ ID NO. 7)

(SEQ ID NO. 7) 5'-tcgaggccaacgtcatcgacttcgaaggttcgaatccttctcttcccaccattttttttcc ccggttgcagtagctgaagcttcaagcttaggaagagaagggtggtaaaaaaaagg ctgaacgtcatcgacttcgaaggttcgaatccttctgctgtcaccagtcgacc-3' gagatgcagtagctgaagcttccaagcttaggaagggacaggtggtcagctggagct-5' (SEQ ID NO. 34)

Egs 4/4 (SEQ ID NO. 8)

(SEQ ID NO. 8) 5'-tcgagggctacgtcatcgacttcgaaggttcgaatccttcttgcttcaccattttttt cccgatgcagtagctgaatgcttccaagcttaggaagaacgaagtggtaaaaaa ctgaacgtcatcgacttcgaaggttcgaatccttctgctgtcaccagtcgacc-3' gagatgcagtagctgaagcttccaagcttaggaagggacaggtggtcagctggagct-5' (SEQ ID NO. 35)

Egs 5/5A (SEQ ID NO. 9)

SEQ ID NO. 8) 5'-tcgagtataacgtcatcgacttcgaaggttcgaatccttcaccggtcaccattttttttata catattgcagtagctgaagcttcaagcttaggaagtggccagtggtaaaaaaatat acgtcatcgacttcgaaggttcgaatccttcttcttacaccagtcgacc-3' tgcagtagctgaagcttccaagcttaggaagaagaatgtggtcagctggagct-5' (SEQ ID NO. 36)

Egs 6/6A (SEQ ID NO. 10)

(SEQ ID NO. 10) 5'-tcgagggctacgtcatcgacttcgaaggttcgaatccttcttgcttcaccattttttt cccgatgcagtagctgaatgcttccaagcttaggaagaacgaagtggtaaaaaa acgtcatcgacttcgaaggttcgaatccttcttcttacaccagtcgacc-3' tgcagtagctgaagcttccaagcttaggaagatccgggtggtcagctgcgtacggagct-5' (SEQ ID NO. 37)

The pH4DOZENEGS—vector may be used to both deliver and express the example EGS sequences to appropriate eukaryotic cells in a manner as described for ribozymes in reference examples 1, 2 and 3 whereby the use of a codon optimised gag/pol and env genes would prevent EGSs from targeting these genes during viral production. The inclusion of the EGS sequences into an HIV derived vector will not only allow expression of such sequences in the target cell but also packaging and transfer of such therapeutic sequences by the patient's own HIV. These example EGS sequences target HIV RNA for cleavage by RNAse P. This example is not limiting and other suitable EGS and derived sequences may also be used; be they expressed singularly, in multiples, from pol I pol II or pol III promoters and derivatives thereof and/or in combination with other HIV treatments. Other appropriate nucleotide sequences of interest (NOIs) may also be included in combination with EGSs if preferred.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

References

Bender et al., 1987, J Virol 61: 1639–1646.
Chesebro, B., K. Wehrly, and W. Maury. 1990. J Virol. 64:4553–7.
Cosset et al., 1995, J. Virol. 69: 7430–7436.
Foecking, M. K., and H. Hofstetter. 1986. Gene. 45:101–105.
Forster and Altman, 1990, Science 249: 783–786.
Gervaix, A., X. Li, G. Kraus, and F. Wong Staal. 199. J Virol. 71 :3048–53.
Goodchild, J., V. Kohli. 1991. *Arch Biochem Biophys* Feb 1; 284(2):386–391.
Haas, J., E.-C. Park, and B. Seed. 1996. Current Biology. 6:315.
Kawa et al., 1998, RNA 4: 1397–1406.
Kim, V. N., K. Mitrophanous, S. M. Kingsman, and K. A. J. 1998. J Virol 72: 811–816.
Lever, A. M. 1995. Br Med Bull. 51:149–66.
Ma et al., 1998, Antisense and Nucleic Acid Drug Development 8: 415–426.
Ory, D. S., B. A. Neugeboren, and R. C. Mulligan. 1996. Proc Natl Acad Sci U S A. 93:11400–6.
Pear et al., 1993, Proc Natl Acad Sci 90: 8392–8396.
Riddell, S. R., M. Elliott, D. A. Lewinsohn, M. J. Gilbert, L. Wilson, S. A. Manley, S. D.
Lupton, R. W. Overell, T. C. Reynolds, L. Corey, and P. D. Greenberg. 1996. Nat Med. 2:216–23.
Soneoka, Y., P. M. Cannon, E. E. Ramsdale, J. C. Griffiths, G. Romano, S. M. Kingsman, and A. J. Kingsman. 1995. Nucleic Acids Res. 23:628–33.
Spector, D. H., E. Wade, D. A. Wright, V. Koval, C. Clark, D. Jaquish, and S. A. Spector. 1990. J Virol. 64:2298–2308.
Srinivasakumar, N., N. Chazal, C. Helga Maria, S. Prasad, M. L. Hammarskjold, and D. Rekosh. 1997. J Virol. 71 :5841–8.
Valsesia Wittmann, S., A. Drynda, G. Deleage, M. Aumailiey, J. M. Heard, O. Danos, G.
Verdier, and F. L. Cosset 1994. J Virol. 68:4609–19.
Werner et al., 1997, Nucleic Acids Symposium Series No. 36: 19–21.
Werner et al., 1998, RNA 4: 847–855.
Yu, H., A. B. Rabson, M. Kaul, Y. Ron, and J. P. Dougherty. 1996. J Virol. 70:4530–37.
Yuan and Altman, 1994, Science 263:1269–1273.
Yuan and Altman, 1995, EMBO J. 14: 159–168.
Yuan et al., 1992, Proc Natl Acad Sci 89: 8006–8010.
Zhu, Z. H., S. S. Chen, and A. S. Huang. 1990. J Acquir Immune Defic Syndr. 3:215–9.
Zolotukhin, S., M. Potter, W. W. Hauswirth, J. Guy, and N. Muzyczka. 1996. J Virol. 70:4646–54.

What is claimed:

1. A viral vector system comprising:
   (i) a first nucleotide sequence and a second nucleotide sequence, wherein the first nucleotide sequence encodes an external guide sequence capable of binding to and effecting the cleavage by RNase P of the second nucleotide sequence, or transcription product thereof, wherein the second nucleotide sequence encodes a viral polypeptide required for the assembly of viral particles; and
   (ii) a third nucleotide sequence encoding a viral polypeptide required for the assembly of viral particles, which third nucleotide sequence has a different nucleotide sequence than the second nucleotide sequence, such that the third nucleotide sequence, or transcription product thereof, is resistant to cleavage directed by the external guide sequence.

2. The viral vector system according to claim 1, further comprising at least one further nucleotide sequence encoding a gene product capable of binding to and effecting the cleavage, directly or indirectly, of the second nucleotide sequence, or transcription product thereof, wherein the gene product is selected from an external guide sequence, a ribozyme and an anti-sense ribonucleic acid.

3. A viral vector production system comprising:
   (i) a viral genome comprising at least one first nucleotide sequence and a second nucleotide sequence, wherein the at least one first nucleotide sequence encodes a gene product capable of binding to and effecting the cleavage, directly or indirectly, of the second nucleotide sequence, or transcription product thereof, wherein the second nucleotide sequence encodes a viral polypeptide required for the assembly of viral particles;

(ii) a third nucleotide sequence encoding a viral polypeptide required for the assembly of the viral genome into viral particles, which third nucleotide sequence has a different nucleotide sequence than the second nucleotide sequence such that said third nucleotide sequence, or transcription product thereof, is resistant to cleavage directed by said gene product;

wherein at least one gene product is an external guide sequence capable of binding to and effecting the cleavage by RNase P of the second nucleotide sequence.

4. The viral vector production system according to claim 3, wherein, in addition to an external guide sequence, at least one gene product is selected from a ribozyme and an anti-sense ribonucleic acid.

5. The viral vector system according to claim 1, wherein the viral vector is a retroviral vector.

6. The viral vector system according to claim 5, wherein the retroviral vector is a lentiviral vector.

7. The viral vector system according to claim 6, wherein the lentiviral vector is an HIV vector.

8. The viral vector system according to claim 5, wherein the polypeptide required for the assembly of viral particles is selected from gag, pol and env proteins.

9. The viral vector system according to claim 8, wherein at least the gag and pol proteins are from a lentivirus.

10. The viral vector system according to claim 8, wherein the env protein is from a lentivirus.

11. The viral vector system according to claim 9, wherein the lentivirus is HIV.

12. The viral vector system according to claim 3, wherein the third nucleotide sequence is resistant to cleavage directed by the gene product as a result of one or more conservative alterations in the third nucleotide sequence, which remove cleavage sites recognised by the at least one gene product and/or binding sites for the at least one gene product.

13. The vital vector system according to claim 1, wherein the third nucleotide sequence is adapted to be resistant to cleavage by RNase P.

14. The viral vector system according to claim 1, wherein the third nucleotide sequence is codon optimised for expression in producer cells.

15. The viral vector system according to claim 14, wherein the producer cells are mammalian cells.

16. The viral vector system according to claim 1 comprising a plurality of first nucleotide sequences and third nucleotide sequences as defined in claim 1.

17. A viral particle comprising the viral vector genome as defined in claim 3 and one or more third nucleotide sequences as defined in claim 3.

18. A viral particle produced using the viral vector production system according to claim 3.

19. A method for producing a viral particle which method comprises introducing into a host cell (i) the viral genome as defined in claim 3 (ii) one or more third nucleotide sequences as defined in claim 3 and (iii) nucleotide sequences encoding essential viral packaging components not encoded by the one or more third nucleotide sequences.

20. A viral particle produced by the method of claim 19.

21. A pharmaceutical composition comprising the viral particle according to claim 17, together with a pharmaceutically acceptable carrier or diluent.

22. A method of treating a viral infection, comprising administering to a subject infected with a virus an effective amount of the viral system according to claim 1.

* * * * *

SEQUENCE LISTING

<160> NUMBER OF SEQ ID NOS: 73

<210> SEQ ID NO 1
<211> LENGTH: 4307
<212> TYPE: DNA
<213> ORGANISM: Human immunodeficiency virus type 1

<400> SEQUENCE: 1

```
atgggtgcga gagcgtcagt attaagcggg ggagaattag atcgatggga aaaaattcgg      60
ttaaggccag ggggaaagaa aaatatataaa ttaaaacata tagtatgggc aagcagggag     120
ctagaacgat tcgcagttaa tcctggcctg ttagaaacat cagaaggctg tagacaaata     180
ctgggacagc tacaaccatc ccttcagaca ggatcagaag aacttagatc attatataat     240
acagtagcaa ccctctattg tgtgcatcaa aggatagaga taaaagacac caaggaagct     300
ttagacaaga tagaggaaga gcaaaacaaa agtaagaaaa aagcacagca agcagcagct     360
gacacaggac acagcaatca ggtcagccaa aattacccta tagtgcagaa catccagggg     420
caaatggtac atcaggccat atcacctaga actttaaatg catgggtaaa agtagtagaa     480
gagaaggctt tcagcccaga agtgataccc atgttttcag cattatcaga aggagccacc     540
ccacaagatt taaacaccat gctaaacaca gtggggggac atcaagcagc catgcaaatg     600
ttaaaagaga ccatcaatga ggaagctgca gaatgggata gagtgcatcc agtgcatgca     660
gggcctattg caccaggcca gatgagagaa ccaaggggaa gtgacatagc aggaactact     720
agtacccttc aggaacaaat aggatggatg acaaataatc cacctatccc agtaggagaa     780
atttataaaa gatggataat cctgggatta aataaaatag taagaatgta tagccctacc     840
agcattctgg acataagaca aggaccaaag gaacccttta gagactatgt agaccggttc     900
tataaaactc taagagccga gcaagcttca caggaggtaa aaaattggat gacagaaacc     960
```

-continued

```
ttgttggtcc aaaatgcgaa cccagattgt aagactattt taaaagcatt gggaccagcg    1020
gctacactag aagaaatgat gacagcatgt cagggagtag gaggacccgg ccataaggca    1080
agagttttgg ctgaagcaat gagccaagta acaaattcag ctaccataat gatgcagaga   1140 ggcaattttta ggaaccaaag aaagattgtt aagtgtttca attgtggcaa agaagggcac  1200
acagccagaa attgcagggc ccctaggaaa agggctgtt ggaaatgtgg aaaggaagga    1260
caccaaatga aagattgtac tgagagacag gctaattttt tagggaagat ctggccttcc   1320
tacaagggaa ggccagggaa ttttcttcag agcagaccag agccaacagc cccaccagaa   1380
gagagcttca ggtctggggt agagacaaca actccccctc agaagcagga gccgatagac   1440
aaggaactgt atcctttaac ttccctcagg tcactctttg caacgaccc ctcgtcacaa    1500 taaagatagg gggcaacta aaggaagctc tattagatac aggagcagat gatacagtat    1560
tagaagaaat gagtttgcca ggaagatgga accaaaaat gatagggga attggaggtt    1620 ttatcaaagt aagacagtat gatcagatac tcatagaaat ctgtggacat aaagctatag   1680
gtacagtatt agtaggacct acacctgtca acataattgg aagaaatctg ttgactcaga   1740
ttggttgcac tttaaatttt cccattagcc ctattgagac tgtaccagta aaattaaagc   1800
caggaatgga tggcccaaaa gttaaacaat ggccattgac agaagaaaaa ataaaagcat   1860
tagtagaaat ttgtacagag atggaaaagg aagggaaaat ttcaaaaatt gggcctgaaa   1920
atccatacaa tactccagta tttgccataa agaaaaaaga cagtactaaa tggagaaaat   1980
tagtagattt cagagaactt aataagagaa ctcaagactt ctgggaagtt caattaggaa   2040
taccacatcc cgcagggtta aaaagaaaa aatcagtaac agtactggat gtgggtgatg    2100 catattttc agttcccttta gatgaagact tcaggaagta tactgcattt accataccta   2160
gtataaacaa tgagacacca gggattagat atcagtacaa tgtgcttcca cagggatgga   2220
aaggatcacc agcaatattc caaagtagca tgacaaaaat cttagagcct tttagaaaac   2280
aaaatccaga catagttatc tatcaataca tggatgattt gtatgtagga tctgacttag   2340
aaatagggca gcatagaaca aaaatagagg agctgagaca acatctgttg aggtggggac   2400
ttaccacacc agacaaaaaa catcagaaag aacctccatt cctttggatg ggttatgaac   2460
tccatcctga taaatggaca gtacagccta tagtgctgcc agaaaaagac agctggactg   2520
tcaatgacat acagaagtta gtggggaaat tgaattgggc aagtcagatt tacccaggga   2580
ttaaagtaag gcaattatgt aaactcctta gaggaaccaa agcactaaca gaagtaatac   2640
cactaacaga agaagcagag ctagaactgg cagaaaacag agagattcta aaagaaccag   2700
tacatggagt gtattatgac ccatcaaaag acttaatagc agaaatacag aagcaggggc   2760
aaggccaatg gacatatcaa atttatcaag agccatttaa aaatctgaaa acaggaaaat   2820
atgcaagaat gaggggtgcc cacactaatg atgtaaaaca attaacagag gcagtgcaaa   2880
aaataaccac agaaagcata gtaatatggg gaaagactcc taaatttaaa ctgcccatac   2940
aaaaggaaac atgggaaaca tggtggacag agtattggca agccacctgg attcctgagt   3000
gggagtttgt taatacccct cccttagtga aattatggta ccagttagag aaagaaccca   3060
tagtaggagc agaaaccttc tatgtagatg gggcagctaa cagggagact aaattaggaa   3120
aagcaggata tgttactaat agaggaagac aaaaagttgt cacctaact gacacaacaa    3180 atcagaagac tgagttacaa gcaatttatc tagctttgca ggattcggga ttagaagtaa   3240
acatagtaac agactcacaa tatgcattag gaatcattca agcacaacca gatcaaagtg   3300
```

-continued

```
aatcagagtt agtcaatcaa ataatagagc agttaataaa aaaggaaaag gtctatctgg    3360
catgggtacc agcacacaaa ggaattggag gaaatgaaca agtagataaa ttagtcagtg    3420
ctggaatcag gaaagtacta ttttagatg gaatagataa ggcccaagat gaacatgaga     3480
aatatcacag taattggaga gcaatggcta gtgattttaa cctgccacct gtagtagcaa    3540
aagaaatagt agccagctgt gataaatgtc agctaaaagg agaagccatg catggacaag    3600
tagactgtag tccaggaata tggcaactag attgtacaca tttagaagga aaagttatcc    3660
tggtagcagt tcatgtagcc agtggatata tagaagcaga agttattcca gcagaaacag    3720
ggcaggaaac agcatatttt cttttaaaat tagcaggaag atggccagta aaacaatac     3780 atactgacaa tggcagcaat ttcaccggtg ctacggttag ggccgcctgt tggtgggcgg    3840
gaatcaagca ggaatttgga attccctaca atcccccaaag tcaaggagta gtagaatcta   3900
tgaataaaga attaaagaaa attataggac aggtaagaga tcaggctgaa catcttaaga    3960
cagcagtaca aatggcagta ttcatccaca attttaaaag aaaaggggggg attgggggt    4020 acagtgcagg ggaaagaata gtagacataa tagcaacaga catacaaact aaagaattac    4080
aaaaacaaat tacaaaaatt caaaattttc gggtttatta cagggacagc agaaattcac    4140
tttggaaagg accagcaaag ctcctctgga aaggtgaagg ggcagtagta atacaagata    4200
atagtgacat aaaagtagtg ccaagaagaa aagcaaagat cattagggat tatggaaaac    4260
agatggcagg tgatgattgt gtggcaagta gacaggatga ggattag                 4307
```

<210> SEQ ID NO 2
<211> LENGTH: 4307
<212> TYPE: DNA
<213> ORGANISM: Artificial Sequence
<220> FEATURE:
<223> OTHER INFORMATION: Description of Artificial Sequence:
gagpol-SYNgp-codon optimised gagpol sequence

<400> SEQUENCE: 2

```
atgggcgccc gcgccagcgt gctgtcgggc ggcgagctgg accgctggga aagatccgc     60 ctgcgccccg gcggcaaaaa gaagtacaag ctgaagcaca tcgtgtgggc cagccgcgaa    120
ctggagcgct tcgccgtgaa ccccgggctc ctggagacca gcgagggtgt gccgccagatc   180 ctcggccaac tgcagcccag cctgcaaacc ggcagcgagg agctgcgcag cctgtacaac    240
accgtggcca cgctgtactg cgtccaccag cgcatcgaaa tcaaggatac gaaagaggcc    300
ctggataaaa tcgaagagga cagaataag agcaaaaaga aggcccaaca ggccgccgcg    360
gacaccggac acagcaacca ggtcagccag aactacccca tcgtgcagaa catccagggg    420
cagatggtgc accaggccat ctcccccgc acgctgaacg cctgggtgaa ggtggtggaa    480
gagaaggctt ttagcccgga ggtgataccc atgttctcag ccctgtcaga gggagccacc    540 cccaagatc tgaacaccat gctcaacaca gtgggggggac accaggccgc catgcagatg    600
ctgaaggaga ccatcaatga ggaggctgcc gaatgggatc gtgtgcatcc ggtgcacgca    660
gggcccatcg caccgggcca gatgcgtgag ccacggggct cagacatcgc cggaacgact    720 agtaccctc aggaacagat cggctggatg accaacaacc cacccatccc ggtgggagaa    780
atctacaaaa gctggatcat cctgggcctg aacaagatcg tgcgcatgta tagcccctacc   840 agcatcctgg acatccgcca aggcccgaag gaaccctttc gcgactacgt ggaccggttc    900
tacaaaacgc tccgcgccga gcaggctagc caggaggtga agaactggat gaccgaaaacc   960 ctgctggtcc agaacgcgaa cccggactgc aagacgatcc tgaaggccct gggccccagcg  1020
```

-continued

```
gctaccctag aggaaatgat gaccgcctgt cagggagtgg gcggacccgg ccacaaggca    1080
cgcgtcctgg ctgaggccat gagccaggtg accaactccg ctaccatcat gatgcagcgc    1140
ggcaactttc ggaaccaacg caagatcgtc aagtgcttca actgtggcaa agaagggcac    1200
acagcccgca actgcagggc ccctaggaaa aagggctgct ggaaatgcgg caaggaaggc    1260
caccagatga aagactgtac tgagagacag gctaatttt tagggaagat ctggccttcc    1320
tacaagggaa ggccagggaa ttttcttcag agcagaccag agccaacagc cccaccagaa    1380
gagagcttca ggtctggggt agagacaaca actcccctc agaagcagga gccgatagac    1440
aaggaactgt atcctttaac ttccctcaga tcactctttg caacgaccc ctcgtcacaa    1500 taaagatagg ggggcagctc aaggaggctc tcctggacac cggagcagac gacaccgtgc    1560
tggaggagat gtcgttgcca ggccgctgga agccgaagat gatcggggga atcggcggtt    1620
tcatcaaggt gcgccagtat gaccagatcc tcatcgaaat ctgcggccac aaggctatcg    1680
gtaccgtgct ggtgggcccc acacccgtca acatcatcgg acgcaacctg ttgacgcaga    1740
tcggttgcac gctgaacttc cccattagcc ctatcgagac ggtaccggtg aagctgaagc    1800
ccgggatgga cggcccgaag gtcaagcaat ggccattgac agaggagaag atcaaggcac    1860
tggtggagat ttgcacagag atggaaaagg aagggaaaat ctccaagatt gggcctgaga    1920
acccgtacaa cacgccggtg ttcgcaatca agaagaagga ctcgacgaaa tggcgcaagc    1980
tggtggactt ccgcgagctg aacaagcgca cgcaagactt ctgggaggtt cagctgggca    2040
tcccgcaccc cgcagggctg aagaagaaga aatccgtgac cgtactggat gtgggtgatg    2100
cctacttctc cgttcccctg gacgaagact tcaggaagta cactgccttc acaatcccctt    2160 cgatcaacaa cgagacaccg gggattcgat atcagtacaa cgtgctgccc cagggctgga    2220
aaggctctcc cgcaatcttc cagagtagca tgaccaaaat cctggagcct ttccgcaaac    2280
agaaccccga catcgtcatc tatcagtaca tggatgactt gtacgtgggc tctgatctag    2340
agatagggca gcaccgcacc aagatcgagg agctgcgcca gcacctgttg aggtggggac    2400
tgaccacacc cgacaagaag caccagaagg agcctccctt cctctggatg ggttacgagc    2460
tgcaccctga caaatggacc gtgcagccta tcgtgctgcc agagaaagac agctggactg    2520
tcaacgacat acagaagctg gtggggaagt tgaactgggc cagtcagatt tacccaggga    2580
ttaaggtgag gcagctgtgc aaactcctcc gcggaaccaa ggcactcaca gaggtgatcc    2640
ccctaaccga ggaggccgag ctcgaactgg cagaaaaccg agagatccta aaggagcccg    2700
tgcacggcgt gtactatgac ccctccaagg acctgatcgc cgagatccag aagcagggcc    2760
aaggccagtg gacctatcag atttaccagg agcccttcaa gaacctgaag accggcaagt    2820
acgcccggat gaggggtgcc cacactaacg acgtcaagca gctgaccgag gccgtgcaga    2880
agatcaccac cgaaagcatc gtgatctggg gaaagactcc taagttcaag ctgcccatcc    2940
agaaggaaac ctgggaaacc tggtggacag agtattggca ggccacctgg attcctgagt    3000
gggagttcgt caacacccct cccctggtga agctgtggta ccagctggag aaggagccca    3060
tagtgggcgc cgaaaccttc tacgtggatg gggccgctaa cagggagact aagctgggca    3120
aagccggata cgtcactaac cggggcagac agaaggttgt caccctcact gacaccacca    3180 accagaaagac tgagctgcag gccatttacc tcgctttgca ggactcgggc ctggaggtga    3240
acatcgtgac agactctcag tatgccctgg gcatcattca agcccagcca gaccagagtg    3300
agtccgagct ggtcaatcag atcatcgagc agctgatcaa gaaggaaaag gtctatctgg    3360
cctgggtacc cgcccacaaa ggcattggcg gcaatgagca ggtcgacaag ctggtctcgg    3420
```

-continued

```
ctggcatcag gaaggtgcta ttcctggatg gcatcgacaa ggcccaggac gagcacgaga    3480 ataccacag caactggcgg gccatggcta gcgacttcaa cctgcccct gtggtggcca      3540 aagagatcgt ggccagctgt gacaagtgtc agctcaaggg cgaagccatg catggccagg   3600
tggactgtag ccccggcatc tggcaactcg attgcaccca tctggagggc aaggttatcc   3660
tggtagccgt ccatgtggcc agtggctaca tcgaggccga ggtcattccc gccgaaacag   3720
ggcaggagac agcctacttc ctcctgaagc tggcaggccg gtggccagtg aagaccatcc   3780
atactgacaa tggcagcaat ttcaccagtg ctacggttaa ggccgcctgc tgtgggcgg    3840 gaatcaagca ggagttcggg atcccctaca atccccagag tcagggcgtc gtcgagtcta   3900
tgaataagga gttaaagaag attatcggcc aggtcagaga tcaggctgag catctcaaga   3960
ccgcggtcca aatggcggta ttcatccaca atttcaagcg gaaggggggg attgggggt    4020 acagtgcggg ggagcggatc gtggacatca tcgcgaccga catccagact aaggagctgc   4080
aaaagcagat taccaagatt cagaatttcc gggtctacta cagggacagc agaaatcccc   4140
tctggaaagg cccagcgaag ctcctctgga agggtgaggg ggcagtagtg atccaggata   4200
atagcgacat caaggtggtg cccagaagaa aggcgaagat cattagggat tatggcaaac   4260
agatggcggg tgatgattgc gtggcgagca gacaggatga ggattag                 4307
```

<210> SEQ ID NO 3
<211> LENGTH: 2571
<212> TYPE: DNA
<213> ORGANISM: Human immunodeficiency virus type 1

<400> SEQUENCE: 3

```
atgagagtga aggggatcag gaggaattat cagcactggt ggggatgggg cacgatgctc     60
cttgggttat taatgatctg tagtgctaca gaaaaattgt gggtcacagt ctattatggg    120
gtacctgtgt ggaaagaagc aaccaccact ctattttgtg catcagatgc taaagcatat    180
gatacagagg tacataatgt ttgggccaca caagcctgtg tacccacaga ccccaaccca    240
caagaagtag aattggtaaa tgtgacagaa aattttaaca tgtggaaaaa taacatggta    300
gaacagatgc atgaggatat aatcagttta tgggatcaaa gcctaaagcc atgtgtaaaa   360
ttaaccccac tctgtgttac tttaaattgc actgatttga ggaatactac taataccaat    420
aatagtactg ctaataacaa tagtaatagc gagggaacaa taaagggagg agaaatgaaa    480
aactgctctt tcaatatcac cacaagcata agagataaga tgcagaaaga atatgcactt    540
ctttataaac ttgatatagt atcaatagat aatgatagta ccagctatag gttgataagt    600
tgtaatacct cagtcattac acaagcttgt ccaaagatat cctttgagcc aattcccata    660
cactattgtg ccccggctgg ttttgcgatt ctaaaatgta acgataaaaa gttcagtgga    720
aaaggatcat gtaaaaatgt cagcacagta caatgtacac atggaattag gccagtagta    780
tcaactcaac tgctgttaaa tggcagtcta gcagaagaag aggtagtaat tagatctgag    840
aatttcactg ataatgctaa aaccatcata gtacatctga tgaatctgt acaaattaat    900 tgtacaagac ccaactacaa taaagaaaa aggatacata taggaccagg gagagcattt    960
tatacaacaa aaaatataat aggaactata agacaagcac attgtaacat tagtagagca   1020
aaatggaatg acactttaag acagatagtt agcaaattaa agaacaatt taagaataaa   1080 acaatagtct ttaatcaatc ctcaggaggg gacccagaaa ttgtaatgca cagttttaat   1140
tgtggagggg aattttttcta ctgtaataca tcaccactgt ttaatagtac ttggaatggt   1200
```

-continued

```
aataatactt ggaataatac tacagggtca aataacaata tcacacttca atgcaaaata    1260
aaacaaatta taaacatgtg gcaggaagta ggaaaagcaa tgtatgcccc tcccattgaa    1320
ggacaaatta gatgttcatc aaatattaca gggctactat taacaagaga tggtggtaag    1380
gacacggaca cgaacgacac cgagatcttc agacctggag gaggagatat gagggacaat    1440
tggagaagtg aattatataa atataaagta gtaacaattg aaccattagg agtagcaccc    1500
accaaggcaa agagaagagt ggtgcagaga gaaaaaagag cagcgatagg agctctgttc    1560
cttgggttct taggagcagc aggaagcact atgggcgcag cgtcagtgac gctgacggta    1620
caggccagac tattattgtc tggtatagtg caacagcaga caatttgctg agggccatt    1680 gaggcgcaac agcatatgtt gcaactcaca gtctgggca tcaagcagct ccaggcaaga    1740
gtcctggctg tggaaagata cctaaaggat caacagctcc tggggttttg gggttgctct    1800
ggaaaactca tttgcaccac tactgtgcct tggaatgcta gttggagtaa taaatctctg    1860
gatgatattt ggaataacat gacctggatg cagtgggaaa gagaaattga caattacaca    1920
agcttaatat actcattact agaaaaatcg caaacccaac aagaaaagaa tgaacaagaa    1980
ttattggaat tggataaatg gcaagttttg tggaattggt ttgacataac aaattggctg    2040
tggtatataa aaatattcat aatgatagta ggaggcttgg taggtttaag aatagttttt    2100
gctgtacttt ctatagtgaa tagagttagg cagggatact caccattgtc gttgcagacc    2160
cgccccccag ttccgagggg acccgacagg cccgaaggaa tcgaagaaga aggtggagag    2220
agagacagag acacatccgg tcgattagtg catggattct tagcaattat ctgggtcgac    2280
ctgcggagcc tgttcctctt cagctaccac cacagagact tactcttgat tgcagcgagg    2340
attgtggaac ttctgggacg caggggtgg gaagtcctca aatattggtg gaatctccta    2400
cagtattgga gtcaggaact aaagagtagt gctgttagct tgcttaatgc cacagctata    2460
gcagtagctg aggggacaga tagggttata gaagtactgc aaagagctgg tagagctatt    2520
ctccacatac ctacaagaat aagacagggc ttggaaaggg ctttgctata a             2571
```

<210> SEQ ID NO 4
<211> LENGTH: 2571
<212> TYPE: DNA
<213> ORGANISM: Artificial Sequence
<220> FEATURE:
<223> OTHER INFORMATION: Description of Artificial Sequence:
    SYNgp-160mn-codon optimised env sequence

<400> SEQUENCE: 4

```
atgagggtga agggatccg ccgcaactac cagcactggt ggggctgggg cacgatgctc     60
ctggggctgc tgatgatctg cagcgccacc gagaagctgt gggtgaccgt gtactacggc    120
gtgcccgtgt ggaaggaggc caccaccacc ctgttctgcg ccagcgacgc caaggcgtac    180
gacaccgagg tgcacaacgt gtgggccacc caggcgtgcg tgcccaccga ccccaacccc    240
caggaggtgg agctcgtgaa cgtgaccgag aacttcaaca tgtggaagaa caacatggtg    300
gagcagatgc atgaggacat catcagcctg tgggaccaga gcctgaagcc ctgcgtgaag    360
ctgacccccc tgtgcgtgac cctgaactgc accgacctga ggaacaccac caacaccaac    420
aacagcaccg ccaacaacaa cagcaacagc gagggcacca tcaagggcgg cgagatgaag    480
aactgcagct tcaacatcac caccagcatc cgcgacaaga tgcagaagga gtacgccctg    540
ctgtacaagc tggatatcgt gagcatcgac aacgacagca ccagctaccg cctgatctcc    600
tgcaacacca gcgtgatcac ccaggcctgc cccaagatca gcttcgagcc catccccatc    660
```

```
cactactgcg cccccgccgg cttcgccatc ctgaagtgca acgacaagaa gttcagcggc    720
aagggcagct gcaagaacgt gagcaccgtg cagtgcaccc acggcatccg gccggtggtg    780
agcacccagc tcctgctgaa cggcagcctg gccgaggagg aggtggtgat ccgcagcgag    840
aacttcaccg acaacgccaa gaccatcatc gtgcacctga atgagagcgt gcagatcaac    900
tgcacgcgtc ccaactacaa caagcgcaag cgcatccaca tcggcccegg cgcgccttc    960 tacaccacca agaacatcat cggcaccatc cgccaggccc actgcaacat ctctagagcc   1020
aagtggaacg acaccctgcg ccagatcgtg agcaagctga aggagcagtt caagaacaag   1080
accatcgtgt tcaaccagag cagcggcggc gaccccgaga tcgtgatgca cagcttcaac   1140
tgcggcggcg aattcttcta ctgcaacacc agcccctgt tcaacagcac ctggaacggc   1200
aacaacacct ggaacaacac caccggcagc aacaacaata ttaccctcca gtgcaagatc   1260
aagcagatca tcaacatgtg gcaggaggtg ggcaaggcca tgtacgcccc ccccatcgag   1320
ggccagatcc ggtgcagcag caacatcacc ggtctgctgc tgacccgcga cggcggcaag   1380
gacaccgaca ccaacgacac cgaaatcttc cgccccggcg gcggcgacat gcgcgacaac   1440
tggagatctg agctgtacaa gtacaaggtg gtgacgatcg agcccctggg cgtggccccc   1500
accaaggcca agcgccgcgt ggtgcagcgc gagaagcggg ccgccatcgg cgccctgttc   1560
ctgggcttcc tggggcggc gggcagcacc atggggggccg ccagcgtgac cctgaccgtg   1620
caggcccgcc tgctcctgag cggcatcgtg cagcagcaga acaacctcct ccgcgccatc   1680
gaggcccagc agcatatgct ccagctcacc gtgtggggca tcaagcagct ccaggcccgc   1740
gtgctggccg tggagcgcta cctgaaggac cagcagctcc tgggcttctg gggctgctcc   1800
ggcaagctga tctgcaccac cacggtaccc tggaacgcct cctggagcaa caagagcctg   1860
gacgacatct ggaacaacat gacctggatg cagtgggagc gcgagatcga taactacacc   1920
agcctgatct acagcctgct ggagaagagc cagacccagc aggagaagaa cgagcaggag   1980
ctgctggagc tggacaagtg ggcgagcctg tggaactggt tcgacatcac caactggctg   2040
tggtacatca aaatcttcat catgattgtg ggcggcctgg tgggcctccg catcgtgttc   2100
gccgtgctga gcatcgtgaa ccgcgtgcgc cagggctaca gccccctgag cctccagacc   2160
cggccccccg tgccgcgcgg gcccgaccgc cccgagggca tcgaggagga gggcggcgag   2220
cgcgaccgcg acaccagcgg caggctcgtg cacggcttcc tggcgatcat ctgggtcgac   2280
ctccgcagcc tgttcctgtt cagctaccac caccgcgacc tgctgctgat cgccgcccgc   2340
atcgtggaac tcctaggccg ccgcggctgg gaggtgctga gtactggtg gaacctcctc   2400 cagtattgga gccaggagct gaagtccagc gccgtgagcc tgctgaacgc caccgccatc   2460
gccgtggccg agggcaccga ccgcgtgatc gaggtgctcc agagggccgg gagggcgatc   2520
ctgcacatcc ccacccgcat ccgccagggg ctcgagaggg cgctgctgta a            2571
```

<210> SEQ ID NO 5
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
tcgagcccgg ggatgacgtc atcgacttcg aaggttcgaa tccttctact gccaccattt     60
tttctctacg tcatcgactt cgaaggttcg aatccttccc tgtccaccag tcgacc         116
```

<210> SEQ ID NO 6
<211> LENGTH: 110
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
tcgagtatta cgtcatcgac ttcgaaggtt cgaatccttc tagattcacc atttttagg       60 aacgtcatcg acttcgaagg ttcgaatcct tccagttcca ccagtcgacc              110

<210> SEQ ID NO 7
<211> LENGTH: 110
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
tcgaggccaa cgtcatcgac ttcgaaggtt cgaatccttc tcttcccacc attttttttc     60
cacgtcatcg acttcgaagg ttcgaatcct tcggggccca ccagtcgacc              110

<210> SEQ ID NO 8
<211> LENGTH: 110
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
tcgagggcta cgtcatcgac ttcgaaggtt cgaatccttc ttgcttcacc attttttctg     60
aacgtcatcg acttcgaagg ttcgaatcct tctgctgtca ccagtcgacc              110

<210> SEQ ID NO 9
<211> LENGTH: 110
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
tcgagtataa cgtcatcgac ttcgaaggtt cgaatccttc accggtcacc attttttat      60 aacgtcatcg acttcgaagg ttcgaatcct tcttcttaca ccagtcgacc              110

<210> SEQ ID NO 10
<211> LENGTH: 116
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
tcgaggtaca cgtcatcgac ttcgaaggtt cgaatccttc gtagttcacc attttttgtg     60
cacgtcatcg acttcgaagg ttcgaatcct tctaggccca ccagtcgacg catgcc       116

<210> SEQ ID NO 11
<211> LENGTH: 8560
<212> TYPE: DNA

<213> ORGANISM: Artificial Sequence
<220> FEATURE:
<223> OTHER INFORMATION: Description of Artificial Sequence: Synthetic
nucleotide pH4DOZENEGS sequence

<400> SEQUENCE: 11

```
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggctttccc cgtcaagctc taaatcgggg ctcccttta  gggttccgat     180
ttagtgcttt acggcacctc gaccccaaaa aacttgatta gggtgatggt tcacgtagtg     240
ggccatcgcc ctgatagacg gttttttcgcc ctttgacgtt ggagtccacg ttctttaata    300
gtggactctt gttccaaact ggaacaacac tcaaccctat ctcggtctat tcttttgatt    360
tataagggat tttgccgatt tcggcctatt ggttaaaaaa tgagctgatt taacaaaaat    420
ttaacgcgaa ttttaacaaa atattaacgc ttacaatttc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctcca    660
ccgcggtggc ggccgctcta gagtccgtta cataacttac ggtaaatggc ccgcctggct    720
gaccgcccaa cgacccccgc ccattgacgt caataatgac gtatgttccc atagtaacgc    780
caatagggac tttccattga cgtcaatggg tggagtattt acggtaaact gcccacttgg    840
cagtacatca agtgtatcat atgccaagta cgccccctat tgacgtcaat gacggtaaat    900
ggcccgcctg gcattatgcc cagtacatga ccttatggga ctttcctact tggcagtaca    960
tctacgtatt agtcatcgct attaccatgg tgatgcggtt ttggcagtac atcaatgggc   1020
gtggatagcg gtttgactca cggggatttc caagtctcca ccccattgac gtcaatggga   1080
gtttgttttg gcaccaaaat caacgggact ttccaaaatg tcgtaacaac tccgccccat   1140
tgacgcaaat gggcggtagg cgtgtacggt gggaggtcta tataagcaga gctcgtttag   1200
tgaaccggtc tctctggtta gaccagatct gagcctggga gctctctggc taactaggga   1260
acccactgct taagcctcaa taaagcttgc cttgagtgct tcaagtagtg tgtgcccgtc   1320
tgttgtgtga ctctggtaac tagagatccc tcagaccctt ttagtcagtg tggaaaatct   1380
ctagcagtgg cgcccgaaca gggacttgaa agcgaaaggg aaaccagagg agctctctcg   1440
acgcaggact cggcttgctg aagcgcgcac ggcaagaggc gaggggcggc gactggtgag   1500
tacgccaaaa attttgacta gcggaggcta aaggagaga  gatgggtgcg agagcgtcag   1560
tattaagcgg gggagaatta gatcgcgatg ggaaaaaatt cggttaaggc caggggggaaa   1620
gaaaaaatat aaattaaaac atatagtatg ggcaagcagg gagctagaac gattcgcagt   1680
taatcctggc ctgttagaaa catcagaagg ctgtagacaa atactgggac agctacaacc   1740
atcccttcag acaggatcag aagaacttag atcattatat aatacagtag caaccctcta   1800
ttgtgtgcat caaaggttga gataaaagac accaaggaag ctttagacaa gatagaggga   1860
gagcaaaaca aaagtaagaa aaaagcacag caagcagcag ctgacacagg acacagcaat   1920
caggtcagcc aaaattaccc tatagtgcag aacatccagg ggcaaatggt acatcaggcc   1980
atatcaccta gaactttaaa tgcatgggta aagtagtag  aagagaaggc tttcagccca   2040
gaagtgatac ccatgttttc agcattatca gaaggagcca ccccacaaga tttaaacacc   2100
atgctaaaca cagtgggggg acatcaagca gccatgcaaa tgttaaaaga gaccatcaat   2160
```

```
gaggaagctg caggaattcg cctaaaactg cttgtaccaa ttgctattgt aaaaagtgtt    2220
gctttcattg ccaagtttgt ttcataacaa agccttagg catctcctat ggcaggaaga    2280
agcggagaca gcgacgaaga gctcatcaga acagtcagac tcatcaagct tctctatcaa    2340
agcagtaagt agtacatgta acgcaaccta taccaatagt agcaatagta gcattagtag    2400
tagcaataat aatagcaata gttgtgtggt ccatagtaat catagaatat aggaaaatat    2460
taagacaaag aaaaatagac aggttaattg atagactaat agaaagagca gaagacagtg    2520
gcaatgagag tgaaggagaa atatcagcac ttgtggagat gggggtggag atggggcacc    2580
atgctccttg ggatgttgat gatctgtagt gctacagaaa aattgtgggt cacagtctat    2640 tatgggtac ctgtgtggaa ggaagcaacc accactctat tttgtgcatc agatgctaaa    2700
gcatagatct tcagacttgg aggaggagat atgagggaca attggagaag tgaattatat    2760
aaatataaag tagtaaaaat tgaaccatta ggagtagcac ccaccaaggc aaagagaaga    2820
gtggtgcaga gagaaaaaag agcagtggga ataggagctt tgttccttgg gttcttggga    2880
gcagcaggaa gcactatggg cgcagcgtca atgacgctga cggtacaggc cagacaatta    2940
ttgtctggta tagtgcagca gcagaacaat ttgctgaggg ctattgaggc gcaacagcat    3000
ctgttgcaac tcacagtctg ggcatcaag cagctccagg caagaatcct ggctgtggaa    3060
agatacctaa aggatcaaca gctcctgggg atttggggtt gctctggaaa actcatttgc    3120
accactgctg tgccttggaa tgctagttgg agtaataaat ctctggaaca gatctggaat    3180
cacacgacct ggatggagtg ggacagagaa attaacaatt acacaagctt aatacactcc    3240
ttaattgaag aatcgcaaaa ccagcaagaa aagaatgaac aagaattatt ggaattagat    3300
aaatgggcaa gtttgtggaa ttggtttaac ataacaaatt ggctgtggta tataaaatta    3360
ttcataatga tagtaggagg cttggtaggt ttaagaatag ttttgctgt actttctata    3420 gtgaatagag ttaggcaggg atattcacca ttatcgtttc agacccacct cccaaccccg    3480
aggggacccg acaggcccga aggaatagaa gaagaaggtg gagagagaga cagagacaga    3540
tccattcgat tagtgaacgg atccttggca cttatctggg acgatctgcg gagcctgtgc    3600
ctcttcagct accaccgctt gagagactta ctcttgattg taacgaggat tgtggaactt    3660
ctgggacgca gggggtggga agccctcaaa tattggtgga atctcctaca gtattggagt    3720
caggaactaa agaatagtgc tgttagcttg ctcaatgcca cagccatagc agtagctgag    3780
gggacagata gggttataga agtagtacaa ggagcttgta gagctattcg ccacatacct    3840
agaagaataa gacagggctt ggaaaggatt ttgctataag atgggtggca agtggtcaaa    3900
aagtagtgtg attggatggc ctactgtaag ggaaagaatg agacgagctg agccagcagc    3960
agatagggtg ggagcagcat ctcgacgctg caggagtggg aggcacgat ggccgctttg    4020 gtcgaggcgg atccggccat tagccatatt attcattggt tatatagcat aaatcaatat    4080
tggctattgg ccattgcata cgttgtatcc atatcataat atgtacattt atattggctc    4140
atgtccaaca ttaccgccat gttgacattg attattgact agttattaat agtaatcaat    4200 tacgggtca ttagttcata gcccatatat ggagttccgc gttacataac ttacggtaaa    4260
tggcccgcct ggctgaccgc ccaacgaccc ccgcccattg acgtcaataa tgacgtatgt    4320
tcccatagta acgccaatag ggactttcca ttgacgtcaa tgggtggagt atttacggta    4380
aactgcccac ttggcagtac atcaagtgta tcatatgcca agtacgcccc ctattgacgt    4440
caatgacggt aaatggcccg cctggcatta tgcccagtac atgaccttat gggactttcc    4500
tacttggcag tacatctacg tattagtcat cgctattacc atggtgatgc ggttttggca    4560
```

```
gtacatcaat gggcgtggat agcggtttga ctcacgggga tttccaagtc tccaccccat    4620
tgacgtcaat gggagtttgt tttggcacca aaatcaacgg gactttccaa aatgtcgtaa    4680
caactccgcc ccattgacgc aaatggggcgg taggcatgta cggtgggagg tctatataag    4740
cagagctcgt ttagtgaacc gtcagatcgc ctggagacgc catccacgct gttttgacct    4800
ccatagaaga caccgggacc gatccagcct ccgcggcccc aagcttcagc tgctcgagcc    4860
cggggatgac gtcatcgact tcgaaggttc gaatccttct actgccacca ttttttctct    4920
acgtcatcga cttcgaaggt tcgaatcctt ccctgtccac cagtcgagta ttacgtcatc    4980
gacttcgaag gttcgaatcc ttctagattc accattttt aggaacgtca tcgacttcga    5040
aggttcgaat ccttccagtt ccaccagtcg aggccaacgt catcgacttc gaaggttcga    5100
atccttctct tcccaccatt ttttttccac gtcatcgact tcgaaggttc gaatccttcg    5160 ggcccacca gtcgagggct acgtcatcga cttcgaaggt tcgaatcctt cttgcttcac    5220 catttttct gaacgtcatc gacttcgaag gttcgaatcc ttctgctgtc accagtcgag    5280
tataacgtca tcgacttcga aggttcgaat ccttcaccgg tcaccatttt tttataacgt    5340
catcgacttc gaaggttcga atccttcttc ttacaccagt cgaggtacac gtcatcgact    5400
tcgaaggttc gaatccttcg tagttcacca ttttttgtgc acgtcatcga cttcgaaggt    5460
tcgaatcctt ctaggcccac cagtcgacgc atgcctgcag gtcgaggtcg ataccgtcga    5520
gacctagaaa acatggagc aatcacaagt agcaatacag cagctaccaa tgctgattgt    5580
gcctggctag aagcacaaga ggaggaggag gtgggttttc cagtcacacc tcaggtacct    5640
ttaagaccaa tgacttacaa ggcagctgta gatcttagcc acttttaaa agaaaagggg    5700 ggactggaag ggctaattca ctcccaacga agacaagata tccttgatct gtggatctac    5760
cacacacaag gctacttccc tgattggcag aactacacac cagggccagg gatcagatat    5820
ccactgacct ttggatggtg ctacaagcta gtaccagttg agcaagagaa ggtagaagaa    5880
gccaatgaag agagaacac ccgcttgtta caccctgtga gcctgcatgg gatggatgac    5940
ccggagagag aagtattaga gtggaggttt gacagccgcc tagcatttca tcacatggcc    6000
cgagagctgc atccggagta cttcaagaac tgctgacatc gagcttgcta caagggactt    6060
tccgctgggg actttccagg gaggcgtggc ctgggcggga ctggggagtg cgagccctc    6120 agatgctgca tataagcagc tgcttttgc ctgtactggg tctctctggt tagaccagat    6180
ctgagcctgg gagctctctg gctaactagg gaacccactg cttaagcctc aataaagctt    6240
gccttgagtg cttcaagtag tgtgtgcccg tctgttgtgt gactctggta actagagatc    6300
cctcagaccc ttttagtcag tgtggaaaat ctctagcagt cgaggggggg cccggtaccc    6360
agcttttgtt ccctttagtg agggttaatt gcgcgcttgg cgtaatcatg gtcatagctg    6420
tttcctgtgt gaaattgtta tccgctcaca attccacaca acatacgagc cggaagcata    6480
aagtgtaaag cctggggtgc ctaatgagtg agctaactca cattaattgc gttgcgctca    6540
ctgcccgctt tccagtcggg aaacctgtcg tgccagctgc attaatgaat cggccaacgc    6600
gcggggagag gcggtttgcg tattgggcgc tcttccgctt cctcgctcac tgactcgctg    6660
cgctcggtcg ttcggctgcg gcgagcggta tcagctcact caaaggcggt aatacggtta    6720
tccacagaat caggggataa cgcaggaaag aacatgtgag caaaaggcca gcaaaaggcc    6780
aggaaccgta aaaaggccgc gttgctggcg ttttccata ggctccgccc ccctgacgag    6840
catcacaaaa atcgacgctc aagtcagagg tggcgaaacc cgacaggact ataaagatac    6900
```

-continued

```
caggcgtttc ccctggaag ctccctcgtg cgctctcctg ttccgaccct gccgcttacc    6960
ggatacctgt ccgcctttct cccttcggga agcgtggcgc tttctcatag ctcacgctgt    7020
aggtatctca gttcggtgta ggtcgttcgc tccaagctgg gctgtgtgca cgaaccccc    7080
gttcagcccg accgctgcgc cttatccggt aactatcgtc ttgagtccaa cccggtaaga    7140
cacgacttat cgccactggc agcagccact ggtaacagga ttagcagagc gaggtatgta    7200
ggcggtgcta cagagttctt gaagtggtgg cctaactacg ctacactag aaggacagta    7260
tttggtatct cgctctgct gaagccagtt accttcggaa aaagagttgg tagctcttga    7320
tccggcaaac aaaccaccgc tggtagcggt ggttttttg tttgcaagca gcagattacg    7380
cgcagaaaaa aaggatctca agaagatcct ttgatcttt ctacggggtc tgacgctcag    7440
tggaacgaaa actcacgtta agggattttg gtcatgagat tatcaaaaag gatcttcacc    7500
tagatccttt taaattaaaa atgaagtttt aaatcaatct aaagtatata tgagtaaact    7560
tggtctgaca gttaccaatg cttaatcagt gaggcaccta tctcagcgat ctgtctattt    7620
cgttcatcca tagttgcctg actccccgtc gtgtagataa ctacgatacg ggagggctta    7680
ccatctggcc ccagtgctgc aatgataccg cgagacccac gctcaccggc tccagattta    7740
tcagcaataa accagccagc cggaagggcc gagcgcagaa gtggtcctgc aactttatcc    7800
gcctccatcc agtctattaa ttgttgccgg gaagctagag taagtagttc gccagttaat    7860
agtttgcgca acgttgttgc cattgctaca ggcatcgtgg tgtcacgctc gtcgtttggt    7920
atggcttcat tcagctccgg ttcccaacga tcaaggcgag ttacatgatc ccccatgttg    7980
tgcaaaaaag cggttagctc cttcggtcct ccgatcgttg tcagaagtaa gttggccgca    8040
gtgttatcac tcatggttat ggcagcactg cataattctc ttactgtcat gccatccgta    8100
agatgctttt ctgtgactgg tgagtactca accaagtcat tctgagaata gtgtatgcgg    8160
cgaccgagtt gctcttgccc ggcgtcaata cgggataata ccgcgccaca tagcagaact    8220
ttaaaagtgc tcatcattgg aaaacgttct tcggggcgaa aactctcaag gatcttaccg    8280
ctgttgagat ccagttcgat gtaacccact cgtgcaccca actgatcttc agcatctttt    8340
actttcacca gcgtttctgg gtgagcaaaa acaggaaggc aaaatgccgc aaaaaaggga    8400
ataagggcga cacggaaatg ttgaatactc atactcttcc ttttcaata ttattgaagc    8460
atttatcagg gttattgtct catgagcgga tacatatttg aatgtattta gaaaaataaa    8520
caaatagggg ttccgcgcac atttccccga aaagtgccac                          8560
```

<210> SEQ ID NO 12
<211> LENGTH: 4642
<212> TYPE: DNA
<213> ORGANISM: Artificial Sequence
<220> FEATURE:
<223> OTHER INFORMATION: Description of Artificial Sequence: pSYNGP2-
      codon optimised HIV-1 gagpol with leader sequence

<400> SEQUENCE: 12

```
gggtctctct ggttagacca gatctgagcc tgggagctct ctggctaact agggaaccca      60
ctgcttaagc ctcaataaag cttgccttga gtgcttcaag tagtgtgtgc ccgtctgttg     120
tgtgactctg gtaactagag atccctcaga cccttttagt cagtgtggaa aatctctagc     180
agtggcgccc gaacagggac ctgaaagcga aaggaaacc agagctctct cgacgcagga     240
ctcggcttgc tgaagcgccc gcacggcaag aggcgagggg cggcgactgg tgagtacgcc     300
aaaaattttg actagcggag gctagaagga gagagatggg cgcccgcgcc agcgtgctgt     360
```

-continued

| | |
|---|---|
| cgggcggcga gctggaccgc tgggagaaga tccgcctgcg ccccggcggc aaaaagaagt | 420 |
| acaagctgaa gcacatcgtg tgggccagcc gcgaactgga gcgcttcgcc gtgaaccccg | 480 |
| ggctcctgga gaccagcgag gggtgccgcc agatcctcgg ccaactgcag cccagcctgc | 540 |
| aaaccggcag cgaggagctg cgcagcctgt acaacaccgt ggccacgctg tactgcgtcc | 600 |
| accagcgcat cgaaatcaag gatacgaaag aggccctgga taaatcgaa gaggaacaga | 660 |
| ataagagcaa aaagaaggcc caacaggccg ccgcggacac cggacacagc aaccaggtca | 720 |
| gccagaacta ccccatcgtg cagaacatcc aggggcagat ggtgcaccag gccatctccc | 780 |
| cccgcacgct gaacgcctgg gtgaaggtgg tggaagagaa ggcttttagc ccggaggtga | 840 |
| tacccatgtt ctcagccctg tcagagggag ccaccccca agatctgaac accatgctca | 900 |
| acacagtggg gggacaccag gccgccatgc agatgctgaa ggagaccatc aatgaggagg | 960 |
| ctgccgaatg ggatcgtgtg catccggtgc acgcagggcc catcgcaccg gccagatgc | 1020 |
| gtgagccacg gggctcagac atcgccgaaa cgactagtac ccttcaggaa cagatcggct | 1080 |
| ggatgaccaa caacccaccc atcccggtgg gagaaatcta caaacgctgg atcatcctgg | 1140 |
| gcctgaacaa gatcgtgcgc atgtatagcc ctaccagcat cctggacatc cgccaaggcc | 1200 |
| cgaaggaacc ctttcgcgac tacgtggacc ggttctacaa aacgctccgc gccgagcagg | 1260 |
| ctagccagga ggtgaagaac tggatgaccg aaacccgct ggtccagaac gcgaacccgg | 1320 |
| actgcaagac gatcctgaag gccctgggcc cagcggctac cctagaggaa atgatgaccg | 1380 |
| cctgtcaggg agtgggcgga cccggccaca aggcacgcgt cctggctgag gccatgagcc | 1440 |
| aggtgaccaa ctccgctacc atcatgatgc agcgcggcaa ctttcggaac caacgcaaga | 1500 |
| tcgtcaagtg cttcaactgt ggcaaagaag gcacacagc ccgcaactgc agggccccta | 1560 |
| ggaaaaaggg ctgttggaaa tgtggaaagg aaggacacca aatgaaagat tgtactgaga | 1620 |
| gacaggctaa ttttttaggg aagatctggc cttcccacaa gggaaggcca gggaatttc | 1680 |
| ttcagagcag accagagcca acagccccac cagaagagag cttcaggttt ggggaagaga | 1740 |
| caacaactcc ctctcagaag caggagccga tagacaagga actgtatcct ttagcttccc | 1800 |
| tcagatcact ctttggcagc gacccctcgt cacaataaag atagggggc agctcaagga | 1860 |
| ggctctcctg gacaccggag cagacgacac cgtgctggag gagatgtcgt tgccaggccg | 1920 |
| ctggaagccg aagatgatcg ggggaatcgg cggtttcatc aaggtgcgcc agtatgacca | 1980 |
| gatcctcatc gaaatctgcg gccacaaggc tatcggtacc gtgctggtgg gccccacacc | 2040 |
| cgtcaacatc atcggacgca acctgttgac gcagatcggt tgcacgctga acttccccat | 2100 |
| tagccctatc gagacggtac cggtgaagct gaagcccggg atggacggcc cgaaggtcaa | 2160 |
| gcaatggcca ttgacagagg agaagatcaa ggcactggtg gagatttgca cagagatgga | 2220 |
| aaaggaaggg aaaatctcca agattgggcc tgagaacccg tacaacacgc cggtgttcgc | 2280 |
| aatcaagaag aaggactcga cgaaatggcg caagctggtg gacttccgcg agctgaacaa | 2340 |
| gcgcacgcaa gacttctggg aggttcagct gggcatcccg caccccgcag ggctgaagaa | 2400 |
| gaagaaatcc gtgaccgtac tggatgtggg tgatgcctac ttctccgttc ccctggacga | 2460 |
| agacttcagg aagtacactg ccttcacaat cccttcgatc aacaacgaga caccggggat | 2520 |
| tcgatatcag tacaacgtgc tgccccaggg ctggaaaggc tctcccgcaa tcttccagag | 2580 |
| tagcatgacc aaaatcctgg agccttccg caaacagaac cccgacatcg tcatctatca | 2640 |
| gtacatggat gacttgtacg tgggctctga tctagagata gggcagcacc gcaccaagat | 2700 |
| cgaggagctg cgccagcacc tgttgaggtg gggactgacc acacccgaca agaagcacca | 2760 |

-continued

```
gaaggagcct ccctccctct ggatgggtta cgagctgcac cctgacaaat ggaccgtgca    2820
gcctatcgtg ctgccagaga aagacagctg gactgtcaac gacatacaga agctggtggg    2880
gaagttgaac tgggccagtc agatttaccc agggattaag gtgaggcagc tgtgcaaact    2940
cctccgcgga accaaggcac tcacagaggt gatccccta accgaggagg ccgagctcga    3000
actggcagaa aaccgagaga tcctaaagga gcccgtgcac ggcgtgtact atgacccctc    3060
caaggacctg atcgccgaga tccagaagca ggggcaaggc cagtggacct atcagattta    3120
ccaggagccc ttcaagaacc tgaagaccgg caagtacgcc cggatgaggg gtgcccacac    3180
taacgacgtc aagcagctga ccgaggccgt gcagaagatc accaccgaaa gcatcgtgat    3240
ctggggaaag actcctaagt tcaagctgcc catccagaag gaaacctggg aaacctggtg    3300
gacagagtat tggcaggcca cctggattcc tgagtgggag ttcgtcaaca cccctcccct    3360
ggtgaagctg tggtaccagc tggagaagga gcccatagtg ggcgccgaaa ccttctacgt    3420
ggatggggcc gctaacaggg agactaagct gggcaaagcc ggatacgtca ctaaccgggg    3480
cagacagaag gttgtcaccc tcactgacac caccaaccag aagactgagc tgcaggccat    3540
ttacctcgct ttgcaggact cgggcctgga ggtgaacatc gtgacagact ctcagtatgc    3600
cctgggcatc attaagccc agccagacca gagtgagtcc gagctggtca atcagatcat    3660
cgagcagctg atcaagaagg aaaaggtcta tctggcctgg gtaccgcc acaaaggcat    3720 tggcggcaat gagcaggtcg acaagctggt ctcggctggc atcaggaagg tgctattcct    3780
ggatggcatc gacaaggccc aggacgagca cgagaaatac cacagcaact ggcgggccat    3840
ggctagcgac ttcaacctgc cccctgtggt ggccaaagag atcgtggcca gctgtgacaa    3900
gtgtcagctc aagggcgaag ccatgcatgg ccaggtggac tgtagccccg gcatctggca    3960
actcgattgc acccatctgg agggcaaggt tatcctggta gccgtccatg tggccagtgg    4020
ctacatcgag gccgaggtca ttcccgccga acagggcag gagacagcct acttcctcct    4080
gaagctggca ggccggtggc cagtgaagac catccatact gacaatggca gcaatttcac    4140
cagtgctacg gttaaggccg cctgctggtg ggcgggaatc aagcaggagt tcgggatccc    4200
ctacaatccc cagagtcagg gcgtcgtcga gtctatgaat aaggagttaa agaagattat    4260
cggccaggtc agagatcagg ctgagcatct caagaccgcg gtccaaatgg cggtattcat    4320
ccacaatttc aagcggaagg gggggattgg gggtacagt gcgggggagc ggatcgtgga    4380
catcatcgcg accgacatcc agactaagga gctgcaaaag cagattacca agattcagaa    4440
tttccgggtc tactacaggg acagcagaaa tccctctgg aaaggcccag cgaagctcct    4500
ctggaagggt gagggggcag tagtgatcca ggataatagc gacatcaagg tggtgcccag    4560
aagaaaggcg aagatcatta gggattatgg caaacagatg gcgggtgatg attgcgtggc    4620
gagcagacag gatgaggatt ag                                            4642
```

<210> SEQ ID NO 13
<211> LENGTH: 4353
<212> TYPE: DNA
<213> ORGANISM: Artificial Sequence
<220> FEATURE:
<223> OTHER INFORMATION: Description of Artificial Sequence: pSYNGP3-
      codon optimised HIV-1 gagpol with leader sequence from
      the major splice donor

<400> SEQUENCE: 13

```
gtgagtacgc caaaaatttt gactagcgga ggctagaagg agagagatgg gcgcccgcgc      60
```

-continued

```
cagcgtgctg tcgggcggcg agctggaccg ctgggagaag atccgcctgc gccccgcgg    120 caaaaagaag tacaagctga agcacatcgt gtgggccagc cgcgaactgg agcgcttcgc    180
cgtgaacccc gggctcctgg agaccagcga ggggtgccgc cagatcctcg gccaactgca    240
gcccagcctg caaaccggca gcgaggagct gcgcagcctg tacaacaccg tggccacgct    300
gtactgcgtc accagcgca tcgaaatcaa ggatacgaaa gaggccctgg ataaaatcga    360
agaggaacag aataagagca aaagaaggc ccaacaggcc gccgcggaca ccggacacag    420
caaccaggtc agccagaact accccatcgt gcagaacatc caggggcaga tggtgcacca    480
ggccatctcc ccccgcacgc tgaacgcctg ggtgaaggtg gtggaagaga aggcttttag    540
cccggaggtg atacccatgt tctcagccct gtcagaggga gccaccccc aagatctgaa    600 caccatgctc aacacagtgg ggggacacca ggccgccatg cagatgctga aggagaccat    660
caatgaggag gctgccgaat gggatcgtgt gcatccggtg cacgcagggc ccatcgcacc    720
gggccagatg cgtgagccac ggggctcaga catcgccgga acgactagta cccttcagga    780
acagatcggc tggatgacca acaacccacc catcccggtg ggagaaatct acaaacgctg    840
gatcatcctg ggcctgaaca agatcgtgcg catgtatagc cctaccagca tcctggacat    900
ccgccaaggc ccgaaggaac cctttcgcga ctacgtggac cggttctaca aaacgctccg    960
cgccgagcag gctagccagg aggtgaagaa ctggatgacc gaaaccctgc tggtccagaa    1020
cgcgaacccg gactgcaaga cgatcctgaa ggccctgggc ccagcggcta ccctagagga    1080
aatgatgacc gcctgtcagg gagtgggcgg acccggccac aaggcacgcg tcctggctga    1140
ggccatgagc caggtgacca actccgctac catcatgatg cagcgcggca actttcggaa    1200
ccaacgcaag atcgtcaagt gcttcaactg tggcaaagaa gggcacacag cccgcaactg    1260
cagggcccct aggaaaaagg gctgttggaa atgtggaaag aaggacacc aaatgaaaga    1320 ttgtactgag agacaggcta attttttagg gaagatctgg ccttcccaca agggaaggcc    1380
agggaatttt cttcagagca gaccagagcc aacagcccca ccagaagaga gcttcaggtt    1440
tggggaagag acaacaactc cctctcagaa gcaggagccg atagacaagg aactgtatcc    1500
tttagcttcc ctcagatcac tctttggcag cgacccctcg tcacaataaa gatagggggg    1560
cagctcaagg aggctctcct ggacaccgga gcagacgaca ccgtgctgga ggagatgtcg    1620
ttgccaggcc gctggaagcc gaagatgatc ggggaatcg gcggtttcat caaggtgcgc    1680
cagtatgacc agatcctcat cgaaatctgc ggccacaagg ctatcggtac cgtgctggtg    1740
ggccccacac ccgtcaacat catcggacgc aacctgttga cgcagatcgg ttgcacgctg    1800
aacttcccca ttagccctat cgagacggta ccggtgaagc tgaagcccgg gatggacggc    1860
ccgaaggtca agcaatggcc attgacagag gagaagatca aggcactggt ggagatttgc    1920
acagagatgg aaaaggaagg gaaaatctcc aagattgggc ctgagaaccc gtacaacacg    1980
ccggtgttcg caatcaagaa gaaggactcg acgaaatggc gcaagctggt ggacttccgc    2040
gagctgaaca gcgcacgca agacttctgg gaggttcagc tgggcatccc gcaccccgca    2100
gggctgaaga agaagaaatc cgtgaccgta ctggatgtgg gtgatgccta cttctccgtt    2160
cccctggacg aagacttcag gaagtacact gccttcacaa tcccttcgat caacaacgag    2220
acaccgggga ttcgatatca gtacaacgtg ctgcccagg gctggaaagg ctctcccgca    2280
atcttccaga gtagcatgac caaaatcctg gagcctttcc gcaaacagaa ccccgacatc    2340
gtcatctatc agtacatgga tgacttgtac gtgggctctg atctagagat agggcagcac    2400
cgcaccaaga tcgaggagct gcgccagcac ctgttgaggt ggggactgac cacacccgac    2460
```

-continued

```
aagaagcacc agaaggagcc tcccttcctc tggatgggtt acgagctgca ccctgacaaa    2520
tggaccgtgc agcctatcgt gctgccagag aaagacagct ggactgtcaa cgacatacag    2580
aagctggtgg ggaagttgaa ctgggccagt cagatttacc cagggattaa ggtgaggcag    2640
ctgtgcaaac tcctccgcgg aaccaaggca ctcacagagg tgatccccct aaccgaggag    2700
gccgagctcg aactggcaga aaaccgagag atcctaaagg agcccgtgca cggcgtgtac    2760 tatgaccccct ccaaggacct gatcgccgag atccagaagc aggggcaagg ccagtggacc    2820
tatcagattt accaggagcc cttcaagaac ctgaagaccg gcaagtacgc ccggatgagg    2880
ggtgcccaca ctaacgacgt caagcagctg accgaggccg tgcagaagat caccaccgaa    2940
agcatcgtga tctggggaaa gactcctaag ttcaagctgc ccatccagaa ggaaacctgg    3000
gaaacctggt ggacagagta ttggcaggcc acctggattc ctgagtggga gttcgtcaac    3060 accccctcccc tggtgaagct gtggtaccag ctggagaagg agcccatagt gggcgccgaa    3120
accttctacg tggatgggggc cgctaacagg gagactaagc tgggcaaagc cggatacgtc    3180
actaaccggg gcagacagaa ggttgtcacc ctcactgaca ccaccaacca gaagactgag    3240
ctgcaggcca tttacctcgc tttgcaggac tcgggcctgg aggtgaacat cgtgacagac    3300
tctcagtatg ccctgggcat cattcaagcc cagccagacc agagtgagtc cgagctggtc    3360
aatcagatca tcgagcagct gatcaagaag gaaaaggtct atctggcctg ggtacccgcc    3420
cacaaaggca ttggcggcaa tgagcaggtc gacaagctgg tctcggctgg catcaggaag    3480
gtgctattcc tggatggcat cgacaaggcc caggacgagc acgagaaata ccacagcaac    3540
tggcgggcca tggctagcga cttcaacctg ccccctgtgg tggccaaaga gatcgtggcc    3600
agctgtgaca agtgtcagct caagggcgaa gccatgcatg ccaggtggac tgtagcccc    3660 ggcatctggc aactcgattg cacccatctg gagggcaagg ttatcctggt agccgtccat    3720
gtggccagtg gctacatcga ggccgaggtc attcccgccg aaacagggca ggagacagcc    3780
tacttcctcc tgaagctggc aggccggtgg ccagtgaaga ccatccatac tgacaatggc    3840
agcaatttca ccagtgctac ggttaaggcc gcctgctggt gggcgggaat caagcaggag    3900
ttcgggatcc cctacaatcc ccagagtcag ggcgtcgtcg agtctatgaa taaggagtta    3960
aagaagatta tcggccaggt cagagatcag gctgagcatc tcaagaccgc ggtccaaatg    4020
gcggtattca tccacaattt caagcggaag ggggggattg gggggtacag tgcggggggag    4080 cggatcgtgg acatcatcgc gaccgacatc cagactaagg agctgcaaaa gcagattacc    4140
aagattcaga atttccgggt ctactacagg gacagcagaa atcccctctg gaaaggccca    4200
gcgaagctcc tctggaaggg tgaggggggca gtagtgatcc aggataatag cgacatcaag    4260
gtggtgccca agaaaggc gaagatcatt agggattatg gcaaacagat ggcgggtgat    4320
gattgcgtgg cgagcagaca ggatgaggat tag    4353
```

<210> SEQ ID NO 14
<211> LENGTH: 4327
<212> TYPE: DNA
<213> ORGANISM: Artificial Sequence
<220> FEATURE:
<223> OTHER INFORMATION: Description of Artificial Sequence: pSYNGP4-
      codon optimised HIV-1 gagpol with 20bp of the leader
      sequence of HIV-1

<400> SEQUENCE: 14

```
cggaggctag aaggagagag atgggcgccc gcgccagcgt gctgtcgggc ggcgagctgg     60
```

```
accgctggga gaagatccgc ctgcgccccg gcggcaaaaa gaagtacaag ctgaagcaca    120
tcgtgtgggc cagccgcgaa ctggagcgct tcgccgtgaa ccccgggctc ctggagacca    180
gcgaggggtg ccgccagatc ctcggccaac tgcagcccag cctgcaaacc ggcagcgagg    240
agctgcgcag cctgtacaac accgtggcca cgctgtactg cgtccaccag cgcatcgaaa    300
tcaaggatac gaaagaggcc ctggataaaa tcgaagagga acagaataag agcaaaaaga    360
aggcccaaca ggccgccgcg gacaccggac acagcaacca ggtcagccag aactaccca     420 tcgtgcagaa catccagggg cagatggtgc caggccat ctcccccgc acgctgaacg       480 cctgggtgaa ggtggtggaa gagaaggctt ttagcccgga ggtgataccc atgttctcag    540
ccctgtcaga gggagccacc ccccaagatc tgaacaccat gctcaacaca gtggggggac    600
accaggccgc catgcagatg ctgaaggaga ccatcaatga ggaggctgcc gaatgggatc    660
gtgtgcatcc ggtgcacgca gggcccatcg caccgggcca gatgcgtgag ccacggggct    720
cagacatcgc cggaacgact agtacccttc aggaacagat cggctggatg accaacaacc    780
cacccatccc ggtgggagaa atctacaaac gctggatcat cctgggcctg aacaagatcg    840
tgcgcatgta tagccctacc agcatcctgg acatccgcca aggcccgaag gaaccctttc    900
gcgactacgt ggaccggttc tacaaaacgc tccgcgccga gcaggctagc caggaggtga    960
agaactggat gaccgaaacc ctgctggtcc agaacgcgaa cccggactgc aagacgatcc    1020
tgaaggccct gggcccagcg gctaccctag aggaaatgat gaccgcctgt cagggagtgg    1080
gcggacccgg ccacaaggca cgcgtcctgg ctgaggccat gagccaggtg accaactccg    1140
ctaccatcat gatgcagcgc ggcaacttc ggaaccaacg caagatcgtc aagtgcttca    1200
actgtggcaa agaagggcac acagcccgca actgcagggc ccctaggaaa aagggctgtt    1260
ggaaatgtgg aaaggaagga caccaaatga agattgtac tgagagacag gctaattttt    1320
tagggaagat ctggccttcc cacaagggaa ggccagggaa ttttcttcag agcagaccag    1380
agccaacagc cccaccagaa gagagcttca ggtttgggga agagacaaca actccctctc    1440
agaagcagga gccgatagac aaggaactgt atccttagc ttccctcaga tcactctttg     1500
gcagcgaccc ctcgtcacaa taaagatagg ggggcagctc aaggaggctc tcctggacac    1560
cggagcagac gacaccgtgc tgaggagat gtcgttgcca ggccgctgga agccgaagat    1620
gatcggggga atcggcggtt tcatcaaggt gcgccagtat gaccagatcc tcatcgaaat    1680
ctgcggccac aaggctatcg gtaccgtgct ggtgggcccc acaccccgtca acatcatcgg    1740 acgcaacctg ttgacgcaga tcggttgcac gctgaacttc cccattagcc ctatcgagac    1800
ggtaccggtg aagctgaagc ccgggatgga cggcccgaag gtcaagcaat ggccattgac    1860
agaggagaag atcaaggcac tggtggagat ttgcacagag atgaaaagg aagggaaaat    1920 ctccaagatt gggcctgaga acccgtacaa cacgccggtg ttcgcaatca gaagaagga    1980 ctcgacgaaa tggcgcaagc tggtggactt ccgcagctg aacaagcgca cgcaagactt    2040
ctggagggtt cagctgggca tcccgcaccc cgcagggctg aagaagaaga atccgtgac     2100 cgtactggat gtgggtgatg cctacttctc cgttccctg gacgaagact tcaggaagta    2160
cactgccttc acaatccctt cgatcaacaa cgagacaccg gggattcgat atcagtacaa    2220
cgtgctgccc cagggctgga aggctctcc cgcaatcttc cagagtagca tgaccaaaat    2280
cctggagcct ttccgcaaac agaacccga catcgtcatc tatcagtaca tggatgactt    2340
gtacgtgggc tctgatctag agatagggca gcaccgcacc aagatcgagg agctgcgcca    2400
gcacctgttg aggtggggac tgaccacacc cgacaagaag caccagaagg agcctccctt    2460
```

-continued

```
cctctggatg ggttacgagc tgcaccctga caaatggacc gtgcagccta tcgtgctgcc    2520
agagaaagac agctggactg tcaacgacat acagaagctg gtggggaagt tgaactgggc    2580
cagtcagatt tacccaggga ttaaggtgag gcagctgtgc aaactcctcc gcggaaccaa    2640
ggcactcaca gaggtgatcc ccctaaccga ggaggccgag ctcgaactgg cagaaaaccg    2700
agagatccta aaggagcccg tgcacggcgt gtactatgac ccctccaagg acctgatcgc    2760
cgagatccag aagcagggc aaggccagtg gacctatcag atttaccagg agcccttcaa    2820
gaacctgaag accggcaagt acgcccggat gagggggtgcc cacactaacg acgtcaagca    2880
gctgaccgag gccgtgcaga agatcaccac cgaaagcatc gtgatctggg aaagactcc    2940 taagttcaag ctgcccatcc agaaggaaac ctgggaaacc tggtggacag agtattggca    3000
ggccacctgg attcctgagt gggagttcgt caacaccccct ccctggtga agctgtggta    3060 ccagctggag aaggagccca tagtgggcgc cgaaaccttc tacgtggatg gggccgctaa    3120
cagggagact aagctgggca agccggata cgtcactaac cggggcagac agaaggttgt    3180
caccctcact gacaccacca accagaagac tgagctgcag gccatttacc tcgctttgca    3240
ggactcgggc ctggaggtga acatcgtgac agactctcag tatgccctgg gcatcattca    3300
agcccagcca gaccagagtg agtccgagct ggtcaatcag atcatcgagc agctgatcaa    3360
gaaggaaaag gtctatctgg cctgggtacc cgcccacaaa ggcattggcg gcaatgagca    3420
ggtcgacaag ctggtctcgg ctggcatcag gaaggtgcta ttcctggatg gcatcgacaa    3480
ggcccaggac gagcacgaga ataccacag caactggcgg gccatggcta gcgacttcaa    3540
cctgccccct gtggtggcca aagagatcgt ggccagctgt gacaagtgtc agctcaaggg    3600
cgaagccatg catggccagg tggactgtag ccccggcatc tggcaactcg attgcaccca    3660
tctggagggc aaggttatcc tggtagccgt ccatgtggcc agtggctaca tcgaggccga    3720
ggtcattccc gccgaaacag ggcaggagac agcctacttc ctcctgaagc tggcaggccg    3780
gtggccagtg aagaccatcc atactgacaa tggcagcaat ttcaccagtg ctacggttaa    3840
ggccgcctgc tggtgggcgg gaatcaagca ggagttcggg atcccctaca atccccagag    3900
tcagggcgtc gtcgagtcta tgaataagga gttaaagaag attatcggcc aggtcagaga    3960
tcaggctgag catctcaaga ccgcggtcca aatggcggta ttcatccaca atttcaagcg    4020
gaaggggggg attgggggt acagtgcggg ggagcggatc gtggacatca tcgcgaccga    4080
catccagact aaggagctgc aaaagcagat taccaagatt cagaatttcc gggtctacta    4140
cagggacagc agaaatcccc tctggaaagg cccagcgaag ctcctctgga agggtgaggg    4200
ggcagtagtg atccaggata atagcgacat caaggtggtg cccagaagaa aggcgaagat    4260
cattagggat tatggcaaac agatggcggg tgatgattgc gtggcgagca gacaggatga    4320
ggattag                                                              4327
```

<210> SEQ ID NO 15
<211> LENGTH: 22
<212> TYPE: RNA
<213> ORGANISM: Artificial Sequence
<220> FEATURE:
<223> OTHER INFORMATION: Description of Artificial Sequence:
      Illustrative helix II sequence

<400> SEQUENCE: 15
cugaugaggc cgaaaggccg aa                                             22

```
<210> SEQ ID NO 16
<211> LENGTH: 22
<212> TYPE: RNA
<213> ORGANISM: Human immunodeficiency virus type 1

<400> SEQUENCE: 16
uaguaagaau guauagcccu ac                                              22

<210> SEQ ID NO 17
<211> LENGTH: 22
<212> TYPE: RNA
<213> ORGANISM: Human immunodeficiency virus type 1

<400> SEQUENCE: 17
aacccagauu guaagacuau uu                                              22

<210> SEQ ID NO 18
<211> LENGTH: 22
<212> TYPE: RNA
<213> ORGANISM: Human immunodeficiency virus type 1

<400> SEQUENCE: 18
uguuucaauu guggcaaaga ag                                              22

<210> SEQ ID NO 19
<211> LENGTH: 22
<212> TYPE: RNA
<213> ORGANISM: Human immunodeficiency virus type 1

<400> SEQUENCE: 19
aaaaagggcu guuggaaaug ug                                              22

<210> SEQ ID NO 20
<211> LENGTH: 22
<212> TYPE: RNA
<213> ORGANISM: Human immunodeficiency virus type 1

<400> SEQUENCE: 20
acgaccccuc gucacaauaa ag                                              22

<210> SEQ ID NO 21
<211> LENGTH: 22
<212> TYPE: RNA
<213> ORGANISM: Human immunodeficiency virus type 1

<400> SEQUENCE: 21
ggaauuggag guuuuaucaa ag                                              22

<210> SEQ ID NO 22
<211> LENGTH: 22
<212> TYPE: RNA
<213> ORGANISM: Human immunodeficiency virus type 1

<400> SEQUENCE: 22
auauuuuuca guucccuuag au                                              22

<210> SEQ ID NO 23
<211> LENGTH: 22
<212> TYPE: RNA
<213> ORGANISM: Human immunodeficiency virus type 1

<400> SEQUENCE: 23
uggaugauuu guauguagga uc                                              22
```

```
<210> SEQ ID NO 24
<211> LENGTH: 22
<212> TYPE: RNA
<213> ORGANISM: Human immunodeficiency virus type 1

<400> SEQUENCE: 24
cuuggauggg guuaugaacu cc                                              22

<210> SEQ ID NO 25
<211> LENGTH: 22
<212> TYPE: RNA
<213> ORGANISM: Human immunodeficiency virus type 1

<400> SEQUENCE: 25
cagcuggacu gucaaugaca ua                                              22

<210> SEQ ID NO 26
<211> LENGTH: 22
<212> TYPE: RNA
<213> ORGANISM: Human immunodeficiency virus type 1

<400> SEQUENCE: 26
aacuuucuau guagaugggg ca                                              22

<210> SEQ ID NO 27
<211> LENGTH: 22
<212> TYPE: RNA
<213> ORGANISM: Human immunodeficiency virus type 1

<400> SEQUENCE: 27
aaggccgccu guuggugggc ag                                              22

<210> SEQ ID NO 28
<211> LENGTH: 22
<212> TYPE: RNA
<213> ORGANISM: Human immunodeficiency virus type 1

<400> SEQUENCE: 28
uaagacagca guacaaaugg ca                                              22

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 29
cagctgctcg agcagctgaa gcttgcatgc                                      30

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 30
gtaagttatg taacggacga tatcttgtct tctt                                 34

<210> SEQ ID NO 31
<211> LENGTH: 37
<212> TYPE: DNA
<213> ORGANISM: Artificial Sequence
```

```
<220> FEATURE:
<223> OTHER INFORMATION: Description of Artificial Sequence: Primer

<400> SEQUENCE: 31
cgcatagtcg acgggcccgc cactgctaga gattttc                              37

<210> SEQ ID NO 32
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tcgaggtcga ctggtggaca gggaaggatt cgaaccttcg aagtcgatga cgtagagaaa      60
aaatggtggc agtagaagga ttcgaacctt cgaagtcgat gacgtcatcc ccgggc        116

<210> SEQ ID NO 33
<211> LENGTH: 110
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tcgaggtcga ctggtggaac tggaaggatt cgaaccttcg aagtcgatga cgttcctaaa      60
aaatggtgaa tcatgaagga ttcgaacctt cgaagtcgat gacgtaatac               110

<210> SEQ ID NO 34
<211> LENGTH: 110
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcgaggtcga ctggtgggcc ccgaaggatt cgaaccttcg aagtcgatga cgtggaaaaa      60
aaatggtggg aagagaagga ttcgaacctt cgaagtcgat gacgttggcc               110

<210> SEQ ID NO 35
<211> LENGTH: 110
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tcgaggtcga ctggtgacag cagaaggatt cgaaccttcg aagtcgatga cgttcagaaa      60
aaatggtgaa gcaagaagga ttcgaacctt cgaagtcgat gacgtagccc               110

<210> SEQ ID NO 36
<211> LENGTH: 110
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tcgaggtcga ctggtgtaag agaaggatt cgaaccttcg aagtcgatga cgttataaaa       60
```

```
aaatggtgac cggtgaagga ttcgaaccct cgaagtcgat gacgttatac         110
```

<210> SEQ ID NO 37
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
tcgaggcatg cgtcgactgg tgggcctaga aggattcgaa ccttcgaagt cgatgacgtg    60
cacaaaaaat ggtgaactac gaaggattcg aaccttcgaa gtcgatgacg tgtacc       116
```

<210> SEQ ID NO 38
<211> LENGTH: 12
<212> TYPE: DNA
<213> ORGANISM: Human immunodeficiency virus type 1

<400> SEQUENCE: 38

```
atgggtgcga ga                                                        12
```

<210> SEQ ID NO 39
<211> LENGTH: 12
<212> TYPE: DNA
<213> ORGANISM: Human immunodeficiency virus type 1

<400> SEQUENCE: 39

```
gatgaggatt ag                                                        12
```

<210> SEQ ID NO 40
<211> LENGTH: 12
<212> TYPE: DNA
<213> ORGANISM: Artificial Sequence
<220> FEATURE:
<223> OTHER INFORMATION: Description of Artificial Sequence:
      gagpol-SYNgp-codon optimised gagpol sequence

<400> SEQUENCE: 40

```
atgggcgccc gc                                                        12
```

<210> SEQ ID NO 41
<211> LENGTH: 12
<212> TYPE: DNA
<213> ORGANISM: Artificial Sequence
<220> FEATURE:
<223> OTHER INFORMATION: Description of Artificial Sequence:
      gagpol-SYNgp-codon optimised gagpol sequence

<400> SEQUENCE: 41

```
gatgaggatt ag                                                        12
```

<210> SEQ ID NO 42
<211> LENGTH: 12
<212> TYPE: DNA
<213> ORGANISM: Human immunodeficiency virus type 1

<400> SEQUENCE: 42

```
atgagagtga ag                                                        12
```

<210> SEQ ID NO 43
<211> LENGTH: 12
<212> TYPE: DNA
<213> ORGANISM: Human immunodeficiency virus type 1

-continued

<400> SEQUENCE: 43
gctttgctat aa 12

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence:
SYNgp-160nm-codon optimised env sequence

<400> SEQUENCE: 44
atgagggtga ag 12

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence:
SYNgp-160nm-codon optimised env sequence

<400> SEQUENCE: 45
gcgctgctgt aa 12

<210> SEQ ID NO 46
<211> LENGTH: 34
<212> TYPE: RNA
<213> ORGANISM: Human immunodeficiency virus type 1

<400> SEQUENCE: 46
ggcucgaacu ugucgugguu aucguggaug uguc 34

<210> SEQ ID NO 47
<211> LENGTH: 63
<212> TYPE: RNA
<213> ORGANISM: Artificial Sequence
<220> FEATURE:
<223> OTHER INFORMATION: Description of Artificial Sequence: EGS based
on Tyrosol t-RNA

<400> SEQUENCE: 47
cgauagcaga cucuaaaucu gccgucaucg acuucgaagg uucgaauccu ucccaggaca 60
cca 63

<210> SEQ ID NO 48
<211> LENGTH: 66
<212> TYPE: RNA
<213> ORGANISM: Artificial Sequence
<220> FEATURE:
<223> OTHER INFORMATION: Description of Artificial Sequence: Consensus
EGS sequence
<221> NAME/KEY: modified_base
<222> LOCATION: (1)..(7)
<223> OTHER INFORMATION: Any nucleotide
<221> NAME/KEY: modified_base
<222> LOCATION: (56)..(61)
<223> OTHER INFORMATION: Any nucleotide

<400> SEQUENCE: 48
nnnnnnnagc agacucuaaa ucugccguca ucgacuucga agguucgaau ccuucnnnnn 60 ncacca 66

<210> SEQ ID NO 49

-continued

```
<211> LENGTH: 49
<212> TYPE: RNA
<213> ORGANISM: Artificial Sequence
<220> FEATURE:
<223> OTHER INFORMATION: Description of Artificial Sequence: Consensus
      EGS sequence
<221> NAME/KEY: modified_base
<222> LOCATION: (1)..(7)
<223> OTHER INFORMATION: Any nucleotide
<221> NAME/KEY: modified_base
<222> LOCATION: (39)..(44)
<223> OTHER INFORMATION: Any nucleotide

<400> SEQUENCE: 49
nnnnnnnacg ucaucgacuu cgaagguucg aauccuucnn nnnncacca              49

<210> SEQ ID NO 50
<211> LENGTH: 13
<212> TYPE: RNA
<213> ORGANISM: Human immunodeficiency virus type 1

<400> SEQUENCE: 50
gggccuauag cac                                                     13

<210> SEQ ID NO 51
<211> LENGTH: 13
<212> TYPE: RNA
<213> ORGANISM: Human immunodeficiency virus type 1

<400> SEQUENCE: 51
gaacuacuag uac                                                     13

<210> SEQ ID NO 52
<211> LENGTH: 13
<212> TYPE: RNA
<213> ORGANISM: Human immunodeficiency virus type 1

<400> SEQUENCE: 52
guaagaaugu aua                                                     13

<210> SEQ ID NO 53
<211> LENGTH: 13
<212> TYPE: RNA
<213> ORGANISM: Human immunodeficiency virus type 1

<400> SEQUENCE: 53
gaccgguucu aua                                                     13

<210> SEQ ID NO 54
<211> LENGTH: 13
<212> TYPE: RNA
<213> ORGANISM: Human immunodeficiency virus type 1

<400> SEQUENCE: 54
gacagcaugu cag                                                     13

<210> SEQ ID NO 55
<211> LENGTH: 13
<212> TYPE: RNA
<213> ORGANISM: Human immunodeficiency virus type 1

<400> SEQUENCE: 55
gaagcaauga gcc                                                     13

<210> SEQ ID NO 56
```

```
<211> LENGTH: 13
<212> TYPE: RNA
<213> ORGANISM: Human immunodeficiency virus type 1

<400> SEQUENCE: 56
gggccccuag gaa                                                              13

<210> SEQ ID NO 57
<211> LENGTH: 13
<212> TYPE: RNA
<213> ORGANISM: Human immunodeficiency virus type 1

<400> SEQUENCE: 57
gggaagaucu ggc                                                              13

<210> SEQ ID NO 58
<211> LENGTH: 13
<212> TYPE: RNA
<213> ORGANISM: Human immunodeficiency virus type 1

<400> SEQUENCE: 58
ggaacuguau ccu                                                              13

<210> SEQ ID NO 59
<211> LENGTH: 13
<212> TYPE: RNA
<213> ORGANISM: Human immunodeficiency virus type 1

<400> SEQUENCE: 59
gaaucuauga aua                                                              13

<210> SEQ ID NO 60
<211> LENGTH: 13
<212> TYPE: RNA
<213> ORGANISM: Human immunodeficiency virus type 1

<400> SEQUENCE: 60
ggacagguaa gag                                                              13

<210> SEQ ID NO 61
<211> LENGTH: 13
<212> TYPE: RNA
<213> ORGANISM: Human immunodeficiency virus type 1

<400> SEQUENCE: 61
ggcaguauuc auc                                                              13

<210> SEQ ID NO 62
<211> LENGTH: 46
<212> TYPE: DNA
<213> ORGANISM: Artificial Sequence
<220> FEATURE:
<223> OTHER INFORMATION: Description of Combined DNA/RNA Molecule: Anti-
      HIV EGS construct
<223> OTHER INFORMATION: Description of Artificial Sequence: Anti-HIV
      EGS construct

<400> SEQUENCE: 62
gtgcacguca ucgacuucga agguucgaau ccuucuaggc ccacca                          46

<210> SEQ ID NO 63
<211> LENGTH: 46
<212> TYPE: DNA
<213> ORGANISM: Artificial Sequence
<220> FEATURE:
```

```
<223> OTHER INFORMATION: Description of Combined DNA/RNA Molecule: Anti-
      HIV EGS construct
<223> OTHER INFORMATION: Description of Artificial Sequence: Anti-HIV
      EGS construct

<400> SEQUENCE: 63
gtacacguca ucgacuucga agguucgaau ccuucguagu ucacca                46

<210> SEQ ID NO 64
<211> LENGTH: 46
<212> TYPE: RNA
<213> ORGANISM: Artificial Sequence
<220> FEATURE:
<223> OTHER INFORMATION: Description of Artificial Sequence: Anti-HIV
      EGS construct

<400> SEQUENCE: 64
uauaacguca ucgacuucga agguucgaau ccuucuucuu acacca                46

<210> SEQ ID NO 65
<211> LENGTH: 46
<212> TYPE: RNA
<213> ORGANISM: Artificial Sequence
<220> FEATURE:
<223> OTHER INFORMATION: Description of Artificial Sequence: Anti-HIV
      EGS construct

<400> SEQUENCE: 65
uauaacguca ucgacuucga agguucgaau ccuucaccgg ucacca                46

<210> SEQ ID NO 66
<211> LENGTH: 46
<212> TYPE: RNA
<213> ORGANISM: Artificial Sequence
<220> FEATURE:
<223> OTHER INFORMATION: Description of Artificial Sequence: Anti-HIV
      EGS construct

<400> SEQUENCE: 66
cugaacguca ucgacuucga agguucgaau ccuucugcug ucacca                46

<210> SEQ ID NO 67
<211> LENGTH: 46
<212> TYPE: RNA
<213> ORGANISM: Artificial Sequence
<220> FEATURE:
<223> OTHER INFORMATION: Description of Artificial Sequence: Anti-HIV
      EGS construct

<400> SEQUENCE: 67
ggcuacguca ucgacuucga agguucgaau ccuucuugcu ucacca                46

<210> SEQ ID NO 68
<211> LENGTH: 46
<212> TYPE: DNA
<213> ORGANISM: Artificial Sequence
<220> FEATURE:
<223> OTHER INFORMATION: Description of Combined DNA/RNA Molecule: Anti-
      HIV EGS construct
<223> OTHER INFORMATION: Description of Artificial Sequence: Anti-HIV
      EGS construct

<400> SEQUENCE: 68
ttccacguca ucgacuucga agguucgaau ccuucggggc ccacca                46

<210> SEQ ID NO 69
<211> LENGTH: 46
```

```
-continued

<212> TYPE: RNA
<213> ORGANISM: Artificial Sequence
<220> FEATURE:
<223> OTHER INFORMATION: Description of Artificial Sequence: Anti-HIV
      EGS construct

<400> SEQUENCE: 69
gccaacguca ucgacuucga agguucgaau ccuucucuuc ccacca            46

<210> SEQ ID NO 70
<211> LENGTH: 46
<212> TYPE: RNA
<213> ORGANISM: Artificial Sequence
<220> FEATURE:
<223> OTHER INFORMATION: Description of Artificial Sequence: Anti-HIV
      EGS construct

<400> SEQUENCE: 70
aggaacguca ucgacuucga agguucgaau ccuuccaguu ccacca            46

<210> SEQ ID NO 71
<211> LENGTH: 46
<212> TYPE: RNA
<213> ORGANISM: Artificial Sequence
<220> FEATURE:
<223> OTHER INFORMATION: Description of Artificial Sequence: Anti-HIV
      EGS construct

<400> SEQUENCE: 71
uauuacguca ucgacuucga agguucgaau ccuucuagau ucacca            46

<210> SEQ ID NO 72
<211> LENGTH: 46
<212> TYPE: RNA
<213> ORGANISM: Artificial Sequence
<220> FEATURE:
<223> OTHER INFORMATION: Description of Artificial Sequence: Anti-HIV
      EGS construct

<400> SEQUENCE: 72
cucuacguca ucgacuucga agguucgaau ccuucccugu ccacca            46

<210> SEQ ID NO 73
<211> LENGTH: 46
<212> TYPE: RNA
<213> ORGANISM: Artificial Sequence
<220> FEATURE:
<223> OTHER INFORMATION: Description of Artificial Sequence: Anti-HIV
      EGS construct

<400> SEQUENCE: 73
gaugacguca ucgacuucga agguucgaau ccuucuacug ccacca            46
```